US011504059B2

(12) United States Patent
Geva et al.

(10) Patent No.: US 11,504,059 B2
(45) Date of Patent: Nov. 22, 2022

(54) METHOD, DEVICE AND SYSTEM FOR NON-INVASIVELY MONITORING PHYSIOLOGICAL PARAMETERS

(71) Applicant: G-Medical Innovations Holdings Ltd., Grand Kayman (KY)

(72) Inventors: Nir Geva, Ness Ziona (IL); Yacov Geva, London (GB); Rafi Heumann, Raanana (IL); Shiri Carmielli, Nes-Ziona (IL); Noam Racheli, Hadera (IL); Nimrod Rospsha, Rishon Lezion (IL); Yaron Chen, Hod Hasharon (IL); Tzur Di-Cori, Modiin (IL)

(73) Assignee: G-Medical Innovations Holdings Ltd, Grand Cayman (KY)

( * ) Notice: Subject to any disclaimer, the term of this patent is extended or adjusted under 35 U.S.C. 154(b) by 308 days.

(21) Appl. No.: 16/586,934

(22) Filed: Sep. 28, 2019

(65) Prior Publication Data

US 2020/0163622 A1 May 28, 2020

Related U.S. Application Data

(63) Continuation of application No. 15/225,849, filed on Aug. 2, 2016, now abandoned.
(Continued)

(51) Int. Cl.
*A61B 5/00* (2006.01)
*A61N 1/372* (2006.01)
(Continued)

(52) U.S. Cl.
CPC .......... *A61B 5/6815* (2013.01); *A61B 5/0006* (2013.01); *A61B 5/0008* (2013.01); *A61B 5/0024* (2013.01); *A61B 5/0086* (2013.01); *A61B 5/024* (2013.01); *A61B 5/02055* (2013.01); *A61B 5/02416* (2013.01); *A61B 5/02438* (2013.01); *A61B 5/20* (2013.01); *A61B 5/259* (2021.01); *A61B 5/282* (2021.01); *A61B 5/332* (2021.01); *A61B 5/4836* (2013.01);
(Continued)

(58) Field of Classification Search
CPC ............ A61B 5/02438; A61B 5/02055; A61B 5/0024; A61B 5/0008; A61B 5/0006; A61B 5/282; A61B 5/332; A61B 5/6843; A61B 5/6898; A61B 5/14552; A61N 1/0456; A61N 1/0484; A61N 1/36021; A61N 1/37252; A61N 1/36025
See application file for complete search history.

(56) References Cited

U.S. PATENT DOCUMENTS

| 2013/0215042 A1* | 8/2013 | Messerschmidt .... A61B 5/6898 345/173 |
| 2015/0261412 A1* | 9/2015 | Guillama .............. G06F 3/0482 715/835 |
| 2015/0370384 A1* | 12/2015 | Park ........................ G06F 3/038 345/174 |

\* cited by examiner

*Primary Examiner* — Jon Eric C Morales
(74) *Attorney, Agent, or Firm* — Reches Patents

(57) ABSTRACT

A system for monitoring vital signs, configured to be used in conjunction with a computerized mobile device, the system including: a cover sensor assembly adapted to be operably engaged with the computerized mobile device, the cover sensor assembly having integrated therein at least one physiological sensor; a physiological data acquisition module configured to generate a physiological parameter measurement descriptive of a physical stimulus received by the at least one physiological sensor; and a validation module configured to control a validity status of the physiological parameter measurement.

14 Claims, 11 Drawing Sheets

Related U.S. Application Data

(60) Provisional application No. 62/200,072, filed on Aug. 2, 2015.

(51) Int. Cl.
    *A61N 1/36*     (2006.01)
    *A61N 1/04*     (2006.01)
    *A61B 5/20*     (2006.01)
    *A61B 5/024*     (2006.01)
    *A61B 5/259*     (2021.01)
    *A61B 5/282*     (2021.01)
    *A61B 5/332*     (2021.01)
    *A61B 5/0205*     (2006.01)
    *A61B 5/021*     (2006.01)
    *A61B 5/145*     (2006.01)
    *A61B 5/318*     (2021.01)
    *A61B 5/1455*     (2006.01)

(52) U.S. Cl.
CPC .......... *A61B 5/4848* (2013.01); *A61B 5/6843* (2013.01); *A61B 5/6898* (2013.01); *A61B 5/7221* (2013.01); *A61N 1/0456* (2013.01); *A61N 1/0484* (2013.01); *A61N 1/36021* (2013.01); *A61N 1/36025* (2013.01); *A61N 1/37252* (2013.01); *A61B 5/021* (2013.01); *A61B 5/145* (2013.01); *A61B 5/14551* (2013.01); *A61B 5/14552* (2013.01); *A61B 5/318* (2021.01); *A61B 5/6816* (2013.01); *A61B 2562/222* (2013.01)

510 — SUBJECTING A PHYSIOLOGICAL SENSOR TO A SENSOR STIMULI RELATING TO PHYSIOLOGICAL INFORMATION ABOUT A USER OF A MONITORING SYSTEM AND GENERATING DATA DESCRIPTIVE OF THE SENSOR STIMULI

520 — DETERMINE IF THE CONDITIONS ARE MET FOR DISPLAYINF THE USER THE PHYSIOLOGICAL INFORMATION

530 — DISPLAYING THE USER OF THE MONITORING SYSTEM THE PHYSIOLOGICAL INFORMATION IF THE CONDITIONS ARE MET

FIG. 5

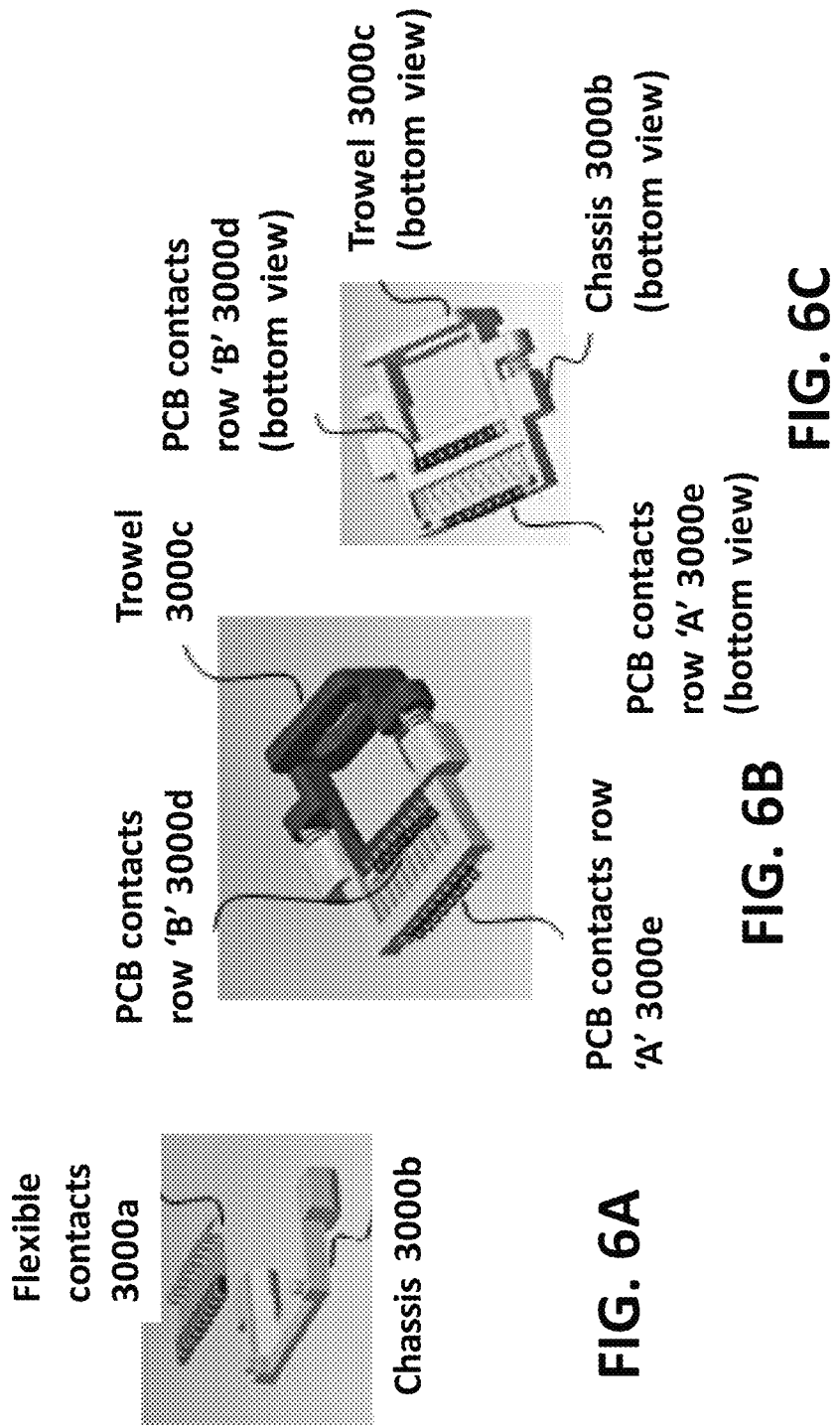

METHOD, DEVICE AND SYSTEM FOR NON-INVASIVELY MONITORING PHYSIOLOGICAL PARAMETERS

FIELD

Embodiments disclosed herein relate in general to the monitoring of physiological parameters of the human body and, particularly, to the noninvasive monitoring of such physiological parameters.

BACKGROUND

A relatively high proportion of the human population suffers from various long term medical conditions such as high blood pressure, cardiac arrhythmia and/or diabetes. These conditions are factors in increased risk of stroke, and yet, many of those suffering from such conditions are not treated properly due to lack of awareness or difficulties in diagnosis. Moreover, large parts of the population live with symptoms which may be indicative of increased likelihood of health conditions such as cardiac ischemia that may lead to Myocardial Infarction (Heart Attack) and other harmful events.

The monitoring of physiological parameters may provide insight to symptoms and can uncover conditions that may develop into adverse health conditions. The description above is presented as a general overview of related art in this field and should not be construed as an admission that any of the information it contains constitutes prior art against the present patent application.

SUMMARY

According to the present invention there is provided a system for monitoring vital signs, configured to be used in conjunction with a computerized mobile device, the system including: a cover sensor assembly adapted to be operably engaged with the computerized mobile device, the cover sensor assembly having integrated therein at least one physiological sensor, a physiological data acquisition module configured to generate a physiological parameter measurement descriptive of a physical stimulus received by the at least one physiological sensor; and a validation module configured to control a validity status of the physiological parameter measurement.

According to further features in preferred embodiments of the invention described below the system further includes at least one validation sensor, positioned so as to be used in conjunction with the at least one physiological sensor and configured to provide validation data to the validation module to determine the validity status of the physiological parameter measurement.

According to still further features in the described preferred embodiments the at least one validation sensor configured to sense whether the at least one physiological sensor is positioned to receive the physical stimulus in a valid manner.

According to still further features the at least one physiological sensor is a photoplethysmograph sensor and the at least one validation sensor is selected from a group of sensors including: a pressure sensor, a position sensor, a capacitance sensor, a conductance sensor.

According to still further features the at least one physiological sensor is selected from the group including: a temperature sensor, a heart rate sensor, an ECG sensor, a photoplethysmograph sensor, a blood pressure sensor and a blood composition sensor.

According to still further features the at least one validation sensor is selected from a group of sensors including: a pressure sensor, a force sensor, a temperature sensor, an impedance sensor, a capacitance sensor, a torque sensor, an accelerometer, a barometer, a light sensor, proximity sensor, a position sensor, a conductance sensor and a humidity sensor.

According to still further features the at least one validation sensor is integrated into the cover sensor assembly.

According to still further features the at least one validation sensor includes a plurality of the validation sensors and at least one of the plurality of validation sensors is integrated into the computerized mobile device operably engaged with the cover sensor assembly. Alternatively, at least one of the plurality of validation sensors is integrated into the cover sensor assembly and at least one of the plurality of validation sensors is integrated into the computerized mobile device operably engaged with the cover sensor assembly.

According to still further features the at least one physiological sensor includes a plurality of the physiological sensors and at least one of the plurality of physiological sensors is integrated in the computerized mobile device.

According to still further features the at least one physiological sensor and/or at least one validation sensor is built into a location on the cover sensor assembly selected from the group including: a backside, a front side and a sidewall.

According to still further features the at least one physiological sensor includes a capacitive sensor.

According to still further features at least one physiological sensor includes a capacitive touch screen of the computerized mobile device.

According to another embodiment there is provided a system for monitoring vital signs, configured to be used in conjunction with a computerized mobile device, the system including: a cover sensor assembly adapted to be operably engaged with the computerized mobile device, the cover sensor assembly having integrated therein an array of conductive elements, each of the conductive elements being electrically isolated from other the conductive elements, such that when a sub-group of the conductive elements are electrically coupled together the sub-group operates as a first physiological sensor; and a physiological data acquisition module configured to generate data descriptive of a physical stimulus received by the first physiological sensor.

According to still further features a second sub-group of the conductive elements operate as a second physiological sensor when the second sub-group of conductive sensors are electrically coupled together and the physiological data acquisition module is further adapted to generate data descriptive of physical stimuli received by the first physiological sensor and the second physiological sensor.

According to still further features a third sub-group of the conductive elements operate as a third physiological sensor when the third sub-group of conductive sensors are electrically coupled together and the physiological data acquisition module is further adapted to generate data descriptive of physical stimuli received by the first, second and third physiological sensors.

According to still further features the array of conductive elements is a line-column array. Alternatively the conductive elements are hexagonal in shape and arranged in a grid formation such that at least one side of each of the hexagonal shaped conductive elements abuts a side of another of the hexagonal shaped conductive elements in the grid formation.

According to another embodiment there is provided a system for monitoring vital signs, configured to be used in conjunction with a computerized mobile device, the system including:

a cover sensor assembly adapted to be operably engaged with the computerized mobile device, the cover sensor assembly having integrated therein an electrical connector port, the electrical connector port having a male-shaped end and a female-shaped end, the male-shaped end adapted to engage a power port of the computerized mobile device and the female-shaped end adapted to receive an external power coupling, the electrical port having a connected state and a disconnected state, wherein in the connected state, the cover sensor assembly is electrically coupled with the computerized mobile device and in the disconnected state, the cover sensor assembly is electrically disconnected from the computerized mobile device; the electrical connector port transforming from the connected state to the disconnected state when the external power coupling is inserted in the female-shaped end of the electrical connector port.

According to still further features the electrical connector port comprises: two power pins and two data pins; wherein the external power coupling, when inserted in the electrical connector port, causes the two power pins to disengage from power couplings of the cover assembly in the electrical connector port, such that the electrical connector port is electrically disconnected from the external power coupling while adapted to be in electrical communication with the computerized mobile device.

BRIEF DESCRIPTION OF THE FIGURES

For simplicity and clarity of illustration, elements shown in the figures may not necessarily been drawn to scale. For example, the dimensions of some of the elements may be exaggerated relative to other elements for clarity of presentation. Furthermore, reference numerals may be repeated among the figures to indicate corresponding or analogous elements. The figures are listed below.

FIG. 5 is a flow chart illustration of a method for measuring and monitoring physiological parameters of a user.

FIG. 6A-C show a switch/disconnecting mechanism for disconnecting sensor electronics;

DETAILED DESCRIPTION

Figure 1A:
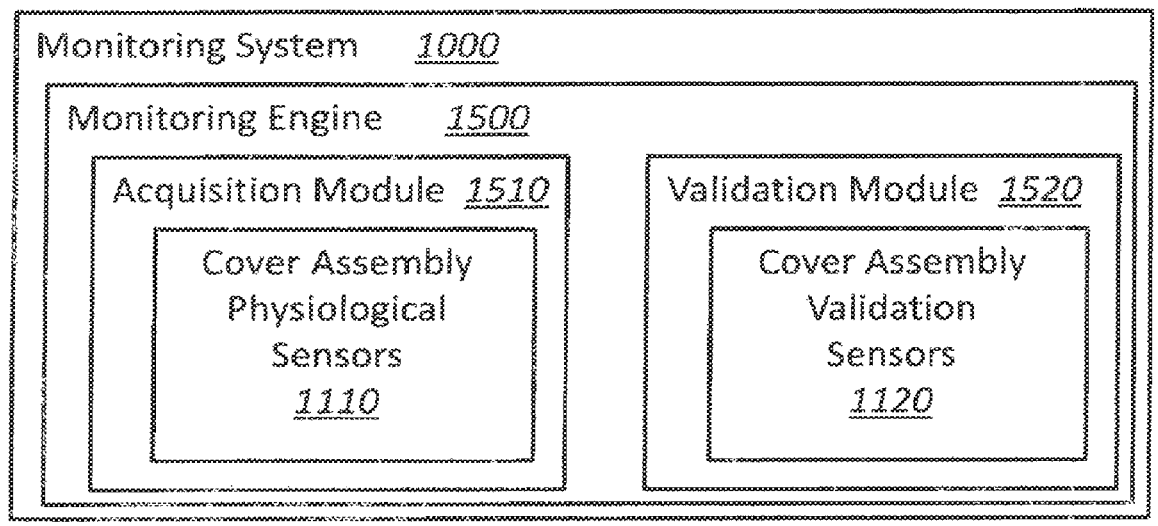
FIG. 1A is a schematic block diagram illustration of a system for monitoring physiological parameters of a user, according to an embodiment.

The following description of a device, system and method for monitoring human physiological parameters is given with reference to particular examples, with the understanding that the device, system and method is not limited to these examples.

Referring to FIGS. 1A-1C and FIGS. 2A-2B, an exemplary embodiment of a monitoring system 1000 for monitoring physiological parameters may include a cover sensor assembly 1100 that can be operably engaged with a computerized mobile device 1200. Monitoring system 1000 may be operative to enable the implementation of a monitoring method, process and/or operation for monitoring physiological parameters of a user of the system.

The term "user" as used herein may refer to a human individual.

Such method, process and/or operation may herein be implemented by a "Monitoring Engine", and may be schematically illustrated as a block referenced by alphanumeric label "1500". The term "engine" as used herein may also relate to and/or include a module and/or a computerized application.

The term "engine" may comprise one or more computer modules, wherein a module may be a self-contained hardware (HW) and/or software (SW) component that interfaces with a larger system (see e.g. Alan Freedman, The Computer Glossary 268, 8$^{th}$ ed., 1998). Such module may be embodied by a circuit or a controller programmed to cause the system to implement a method, process and/or operation as disclosed herein.

A module may comprise a machine and/or machine-executable instructions. For example, a module may be implemented as a HW circuit comprising, e.g., custom very large scale integration (VLSI) circuits or gate arrays, off-the-shelf semiconductor devices such as logic gates, transistors, or other discrete components. A module may also be implemented in programmable HW devices such as field programmable gate arrays, programmable array logic, programmable logic devices or the like.

In an embodiment, monitoring engine 1500 may include a physiological data acquisition module 1510 that generates data ("phy-data") descriptive of a physical stimulus received by a physiological parameter sensor 1140 and which relates to a physiological parameter of a user being monitored, and a validation module 1520 that may determine the status of the validity of the generated phy-data. In an embodiment, monitoring engine 1500 may provide the user only with physiological parameter information for which it is determined by validation module 1520 that the mentioned information is valid.

In an embodiment, monitoring engine 1500 enables monitoring system 1000 to collect and analyze data descriptive of values of a plurality of physiological parameters over time, display graphs to show trends in physiological parameter values and, optionally, alert the user and/or a third party in the event values of a physiological parameter deviate from a normal range (e.g., below or a above a threshold value). Changes in physiological parameters may be displayed to the user of the monitoring system substantially in real-time. In an embodiment, monitoring engine 1500 of system 1000 may automatically analyze and cause the system to provide feedback relating to the physiological information acquired.

Figure 1B:
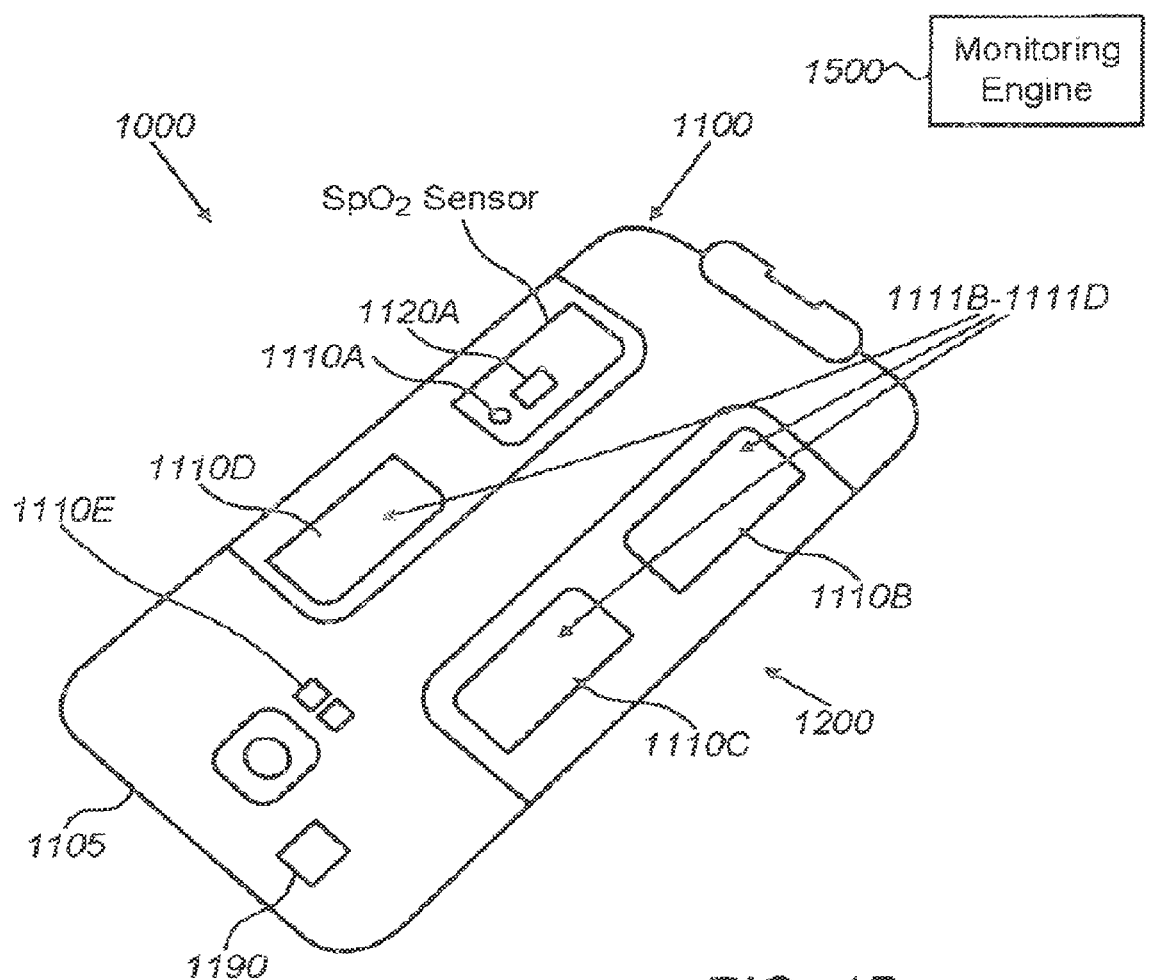
FIG. 1B is a schematic back-view illustration of a sensor assembly installed and operably engaging with a computerized mobile device to form a system for monitoring physiological parameters, according to an embodiment.

Acquisition module 1510 may comprise physiological sensors 1110 that are integrated into cover sensor assembly 1100 (FIG. 1B) and, optionally, in mobile device 1200. Further, validation module 1520 may comprise validation sensors 1120 included in cover sensor assembly 1100 and, optionally in mobile device 1200 (FIG. 1B).

In an embodiment, the sensors of, or comprised in, cover sensor assembly 1100 may be shielded from electromagnetic radiation that may be emitted by mobile device 1200 in order to reduce or eliminate electromagnetic interference to which the sensors of cover sensor assembly 1100 might otherwise be subjected to. The sensors of cover sensor assembly 1100 may thus be operative to measure physiological parameters even during transmission from, and reception of, communication signals by mobile device 1200, for example, when surfing the Web with the mobile device and/or during a telephone call conducted using mobile device 1200.

The expression "measuring physiological parameters" as well as grammatical variations thereof may also encompass the meaning of the term "estimating values of physiological parameters".

A computerized mobile device may, for example, refer to a multifunction mobile end-user device, also known as "cellphone" or "smartphone", a tablet computer, a mini-tablet computer, a personal digital assistant, a handheld computer, and/or a notebook computer.

Cover sensor assembly 1100 may include a cover 1105 suitable to cover or encase, at least partially, mobile device 1200. Cover 1105 has a backside shown schematically in FIGS. 1B-1C, and a front side shown schematically in FIGS. 2A-2B for covering mobile device 1200. Cover 1105 may include a sidewall body portion extending from the edge of the front side to the edge of the cover's backside. In an embodiment, the cover's backside may cover the back of mobile device 1200. The front side may have the form of a rim or frame which, when cover 1105 is installed, rims at least a sufficient portion of the front side of mobile device 1200 so that the device is, at least partially, framed by the cover's backside and rim, coupling the cover to the mobile device. Cover 1105 may be installable on mobile devices 1200 having various shapes and forms. The cover may be sturdy and inflexible or elastically flexible.

Cover sensor assembly 1100 further includes one or more physiological parameter sensors 1110 at the cover's front side (e.g., sensors 1110A-1110E shown in FIGS. 1B and 1C) and one or more physiological parameter sensors at the cover's backside (e.g., sensors 1110Fa and 1110F shown in FIGS. 2A and 2B) for determining a present value of one or more physiological parameters. One or more physiological sensors or interfaces may be located at the sidewall of cover 1105 such as, for example, a "blood-composition" sensor 1110G for measuring glucose and/or cholesterol concentration. Optionally, "blood-composition" sensor 1110G may be operative to determine the blood type sampled by a strip 1111G. Monitoring system 1000 may be operative to enable, for example, transmission of blood-related information including, e.g., glucose level, cholesterol level and/or blood type to a third party, e.g., as outlined herein below in more detail. The transmission of information to a third party may occur responsive to the pressing or engaging of a button 1190 (also referred to as a "panic button") which may be provided by cover sensor assembly 1100 and/or mobile device 1200.

In an embodiment, responsive to engaging panic button 1190, an alarm message is issued to a third party. In an embodiment, monitoring engine 1500 may be configured to filter out unwanted or inadvertent pressing of the panic button, to avoid or reduce the likelihood of false alarms. However, the panic button may be operational even if, for example, mobile device 1200 is in sleep mode, turned off, or locked.

In an embodiment, physiological and/or validation sensors 1110 and/or 1120 may be included in and/or constitute a part of the backside and the front side of cover 1105. For example, physiological sensors 1110A-1110E (FIGS. 1B and 1C), can be included in or constitute a part of the backside of cover 1105, while sensors 1110Fa and 1110F (FIGS. 2A and 2B) may be included in or constitute a part of the front side of cover 1105. Furthermore, physiological and/or validation sensors 1110 and/or 1120 may be included in and/or constitute a part of the cover's sidewall like. e.g., sensor 1110G.

A physiological parameter sensor may in some instances be referred to as "physiological sensor" or "cover physiological sensor".

Cover sensor assembly 1100 may further include one or more validation sensors 1120 at the backside, front side and sidewall of cover 1105. Validation sensors 1120 are positioned so that they can be used in conjunction with physiological parameter sensors 1110 for controlling the validity status of a physiological parameter measurement. For example, the readings of one or more of validation sensors 1120 may be used for determining whether the at least one validation criterion or the conditions for displaying the user with physiological parameter information is/are met. In an embodiment, the readings of a plurality of validation sensors 1120 may be combined together in order to get indication that the physiological measurement will be reliable. The combination, for example, can be defined as using several sensors for indicating that the user holds the device still (threshold over the accelerometer readings), that the user places a finger on a correct position (using conductive sensors), and/or that the pressure of the finger over the sensor is in a correct range (threshold over pressure sensor readings). In an embodiment, the readings of a plurality of validation sensors 1120 may be compared against each other to determine different weightings or to discard readings of physiological sensors 1110 or, in an embodiment to automatically toggle between physiological sensors 1110 acquiring the same physiological parameter. For instance, monitoring engine 1500 may toggle between the reading of acquiring ECG signals and impedance measurements.

In an embodiment, while a user engages a body portion with one or more of the physiological sensors 1110 for determining a present value of a physiological parameter over time, validation sensors 1120 may provide the user with an output indicative of whether the conditions for validly measuring the physiological parameter are met. In another embodiment, only validated information may be displayed to the user. In an embodiment, validation sensors 1120 may be employed for providing instructions to the user on how to engage with physiological sensors 1110 in order to obtain validated values of physiological parameters.

In an embodiment, cover 1105 may include all hardware and/or software required for determining values of physiological parameters and for validating whether the conditions for determining whether a physiological parameter or parameters as/are met. In an embodiment, monitoring engine 1500 may be configured so that mobile device 1200 may only be operative to display to the user physiological information validated by validation module 1520. Accordingly, in an embodiment, mobile device 1200 may be free of physiological and validation sensors 1110 and 1120, which may all be comprised in cover sensor assembly 1100. The expression "displaying information" as well as grammatical variations thereof may, for example, include auditory and/or visual display of information to the user of monitoring system 1000 via, e.g., a speaker (not shown) and/or a screen of mobile device 1200, respectively. The displayed physiological information is descriptive of a physical stimulus to which a physiological sensor was subjected and which relates to a physiological parameter of the user.

When sensor cover assembly 1100 is installed, i.e., operably engaged, physiological sensors 1110 and/or validation sensors 1120 may be communicably coupled with mobile device 1200, e.g., via a communication module (not shown). Communication module may include I/O device drivers (not shown) and/or network interface drivers (not shown) for enabling the transmission and/or reception of data using wired and/or wireless components (not shown). A device driver may, for example, interface with a keypad, a USB port and/or with an audio jack. A network interface driver may for example execute protocols for the Internet, or an Intranet, Wide Area Network (WAN), Local Area Network (LAN) employing, e.g., Wireless Local Area Network (WLAN)), Metropolitan Area Network (MAN), Personal Area Network (PAN), extranet, 2G, 3G, 3.5G, 4G including for example Mobile WIMAX or Long Term Evolution (LTE) advanced, Bluetooth®, ZigBee™, near-field communication (NFC), optical (e.g., IR) communication and/or any other current or future communication network, standard, and/or system.

In an embodiment, at least one of the physiological sensors 1110 may comprise an electrode 1111 on the back of cover 1105. For instance, physiological sensors 1110B-1110D may comprise electrodes 1111B-1111D, respectively, incorporated in mobile device cover 1105 for determining values of bio-impedance parameters, as outlined herein. In an embodiment, a physiological sensor 1110B$_2$ may cover a corner section of cover 1105. In a further example, external validation sensor 1120 may, for example, include a pressure sensor, a force sensor, a temperature sensor, an impedance sensor and/or a capacitance sensor, e.g., located on the back of cover 1105. In an embodiment, electrodes of physiological sensors 1110B to 1110D for example may have a multilayer coating to ensure sufficiently high conductivity without requiring additional moistening of the electrodes. An electrode may for example be a dry electrode with silver or silver chloride coating.

It should be noted that, in some embodiments, the term "front" used herein may refer to the side of mobile device which includes a display, whereas the term "back" may refer to the side of mobile device 1200 which does not have a display. More, specifically, backside of cover 1105 may, when installed, be turned outwardly, i.e., engageable by the user without requiring removal of cover 1105 from mobile device 1200.

Non-limiting examples of physiological sensors 1110 that may be employed by cover sensor assembly 1100 may include an oxygen saturation sensor e.g., for measuring peripheral capillary oxygen saturation (SpO$_2$) and/or for measuring heart rate (both embodied, e.g., by physiological sensor 1110A); a sensor array (e.g., physiological sensors 1110B-1110D) for determining body composition (total body water, for example, to derive body fat/adiposity and/or fat-free mass) and/or cardiac activity for obtaining for instance an electrocardiogram (ECG), electromyography (EMG) and/or Electroencephalography (EEG). An EEG signal may be obtained by operably coupling electrodes (not shown) with mobile device 1200.

Figure 2A:
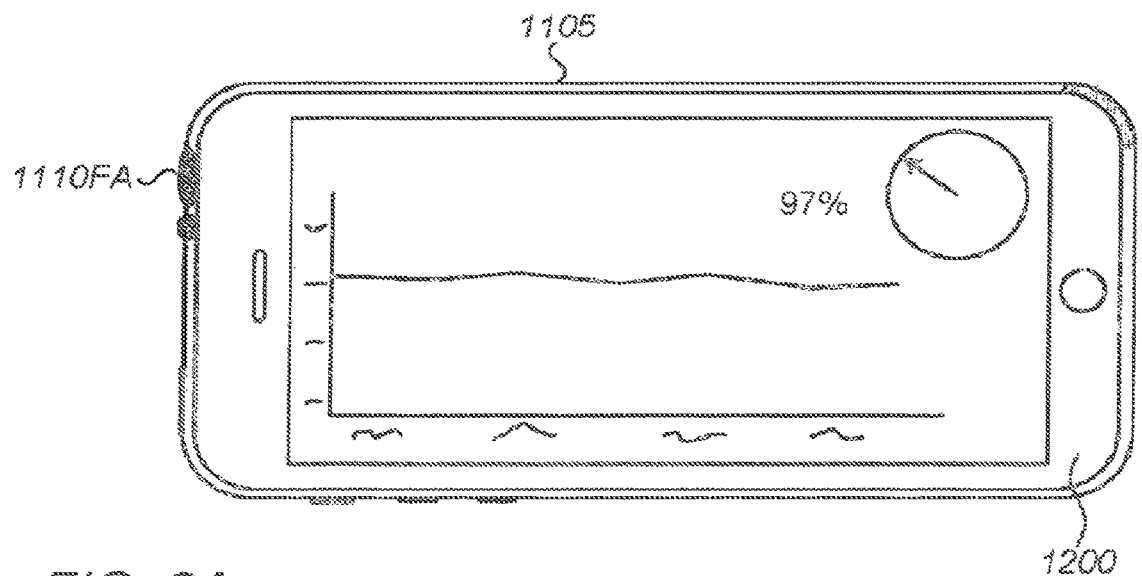
FIG. 2A is a schematic perspective front-view illustration of the sensor assembly and operably engaging with the computerized mobile device, according to an embodiment.
Figure 2B:
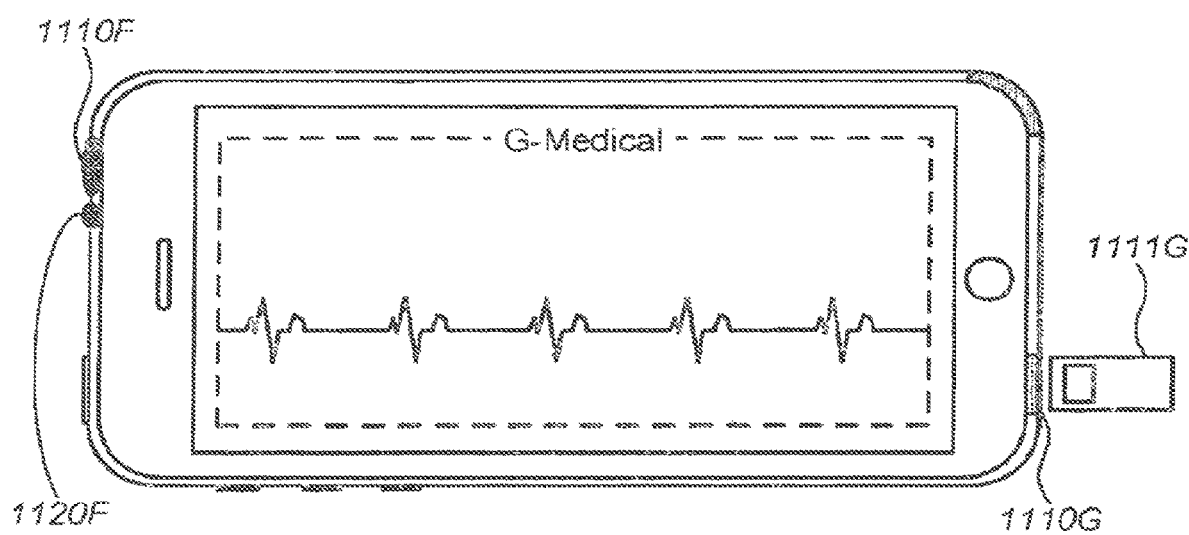
FIG. 2B is another schematic perspective front-view illustration of the sensor assembly and operably engaging with the computerized mobile device, according to an embodiment.

As shown schematically in FIGS. 2A and 2B, a non-contact or contact-based temperature sensor 1110F and 1110Fa for measuring body and/or skin temperature, may be located at the front side of cover 1105. As will be outlined herein below in more detail, temperature sensor 1110F and 1110Fa may be used in conjunction with a temperature validation sensor 1120F.

A non-contact temperature sensor 1110F and 1110Fa may for example be embodied by an infrared radiation (IR) sensor. Such IR-based temperature sensor may comprise a lens or lens arrangement (not shown) for focusing IR radiation onto a detector (not shown) of the IR sensor. The detector converts at least some of the incident energy to an electrical or optical signal that can be represented in units of temperature after being compensated for ambient temperature variation. The measured IR part of Electromagnetic Spectrum may for example span from 0.7 μm to 20 μm wavelengths.

A contact-based temperature sensor 1110F and 1110Fa may be embodied by a thermocouple-based temperature sensor.

By operably positioning for example temperature sensor 1110F and 1110Fa relative to tissue of a body portion of the user like, e.g., the user's forehead or neck an instant value of the user's skin temperature may be determined. For instance, value indicative of the user's skin temperature may be obtained by positioning an IR-based temperature sensor 1110F and 1110Fa such that its detector faces tissue of the user's forehead or neck; or by engaging a contact-based temperature sensor with tissue of the user's forehead or neck.

An estimate about core body temperature may be obtained by sliding temperature sensor 1110F and 1110Fa over various regions of the user's body and by selecting the maximum value from the obtained measurements. The maximum value may be considered to be the core body temperature.

Figure 1C:
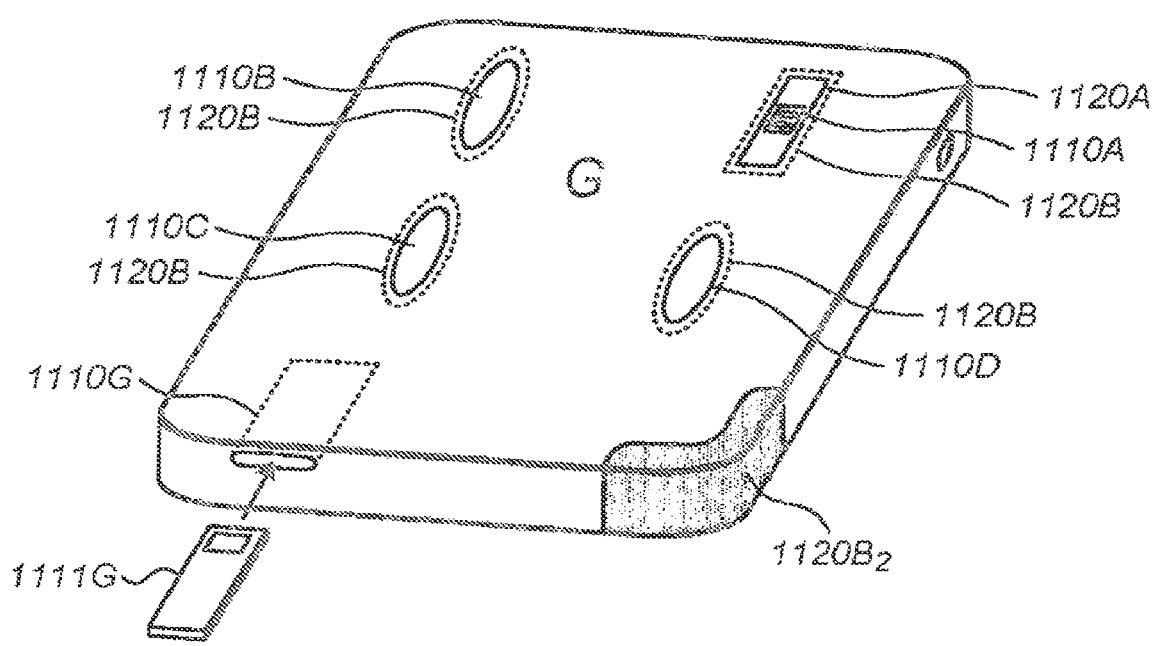
FIG. 1C is another schematic back-view illustration of the sensor assembly and operably engaging with the computerized mobile device, according to an embodiment.

Moreover, in an embodiment, and as schematically shown in FIGS. 1C and 2B cover sensor assembly 1100 may further comprise a sensor 1110G which may have an interface at the sidewall of cover 1105 for allowing receipt of test strips 1111H for the determining glucose and/or cholesterol level in blood and/or blood type for example. Monitoring System 1000 may for example be operative to determine both glucose and cholesterol level from a single test strip via the same interface or via respective glucose- and cholesterol-reading interfaces. In the latter case, by engaging the test strip only once with the sensor, the user may obtain readings both for his/her glucose and the LDL cholesterol level.

In an embodiment, monitoring engine 1500 may be operative to determine the type of test strip engaged with physiological sensor 1110G (glucose or cholesterol test strip) and provide a corresponding output.

The sensor used for glucose measurement may be based on conversion of glucose concentration into a voltage or current signal. Accordingly, the strips may be operative to allow amperometry. In an embodiment, the part of sensor for glucose measurement may comprise a platinum and silver electrode forming part of an electric circuit where hydrogen peroxide is electrolyzed. The hydrogen peroxide is produced as a result of the oxidation of glucose on a glucose oxide membrane. The current through the circuit provides a measurement of the concentration of hydrogen peroxide which, in turn, provides an indication of the glucose concentration on the blood sample of the test strip.

In an embodiment, physiological sensors 1110 may further be operative to obtain values relating to levels of hematocrite, noninvasive glucose, noninvasive blood pressure, blood flow velocity and/or body impedance analyzer. In an embodiment, blood pressure trend may be determined based on pulse transient time (PTT) using signals obtained from the photoplethysmograph and ECG signals.

In an embodiment, some physiological and/or validation sensor 1110 and/or 1120 of cover sensor assembly 1100 may further comprise one or more accelerometers, gyroscopes, torque sensors for measuring a twisting and/or bending force applied on cover 1105 and/or mobile device 1200, barometers, proximity sensors, altimeters, magnetometers, light sensors, touch screen sensors, receivers of a Global Positioning System, a temperature sensor, a barometer, a humidity sensor and/or a front and/or back camera. In an embodiment, an accelerometer may be employed to implement a fall detector, i.e., a detector which identifies an impact by mobile device and/or cover sensor assembly.

In a further example, monitoring system 1000 may include a physiological and/or validation sensor which may be comprised in computerized mobile device 1200. A physiological and/or validation sensor of mobile device 1200 may for example be implemented by the mobile device's inertial sensor and/or by a non-inertial sensor. An inertial sensor may include, for example, an accelerometer, and/or a gyroscope and/or a torque sensor. Non-inertial sensors of mobile device 1200 may include, for example, one or more barometers, proximity sensors, altimeters, magnetometers, light sensors, touch screen sensors, receivers of a Global Positioning System, a temperature sensor, a barometer, a torque sensor for measuring a twisting and/or bending force applied on the mobile device, a humidity sensor and/or a front and/or back camera.

It should be noted that a division made herein of sensors as either being comprised by cover sensor assembly 1100 or comprised by mobile device 1200 should by no means to be construed as limiting. Accordingly, in an embodiment, a first sensor of a plurality of sensors with a particular analogous or identical functionality may be included in mobile device 1200, while a second sensor of the plurality of sensors with the particular functionality may additionally be included or be part of cover sensor assembly 1100. In an embodiment, a sensor which may herein be referred to or listed as being external of mobile device 1200 may in an alternative embodiment be included in mobile device 1200, and vice versa. However, as already indicated herein, in an embodiment, mobile device 1200 may be free of physiological and validation sensors 1110 and 1120, which may all be comprised in cover sensor assembly 1100.

In an embodiment, physiological sensor 1110A, comprised by cover sensor assembly 1100, for the measurement of oxygen saturation sensor and/or heart rate may be implemented by a photoplethysmograph comprising a light-source-photodetector assembly for the emission of light (e.g., at a wavelength or a plurality of wavelengths ranging from 600 nm to 1300 nm) and the detection of light reflected by a body extremity (e.g., a finger) of the user, respectively. In an embodiment, reflectance technique may be employed for the measurement of oxygen saturation sensor and/or heart/pulse rate for example. Correspondingly, the light source and the photodetector are positioned on the same surface, e.g., on the back of cover 1105.

As already briefly mentioned herein, physiological sensors 1110B-1110D may include metallic pads or electrodes. In an embodiment, two of sensors 1110B-1110D may be employed for determining body composition by measuring an electrical parameter (e.g., impedance or conductivity) between two tissue areas of the human body that are positioned distally from one another. Accordingly, determining body composition may be performed based on the principles of Bioelectrical Impedance Analysis (BIA).

For example, a user may bring a tissue area of a finger of a palm (e.g., the index finger) in contact with a first electrode of physiological sensor 1110B and, at the same time, a toe of a foot with a second electrode of physiological sensor 1110C for determining the value of an electrical parameter that is indicative of the impedance imposed by the human body between the two areas to derive body fat concentration. More specifically, body composition may be determined by injecting a small current (e.g., ranging from 0.4-0.8 mA) alternating current into the tissue. The measured voltage difference is translated into impedance. The measured voltage and, hence, the impedance, depends on many factors including, for example, frequency of the alternating current (e.g., 40-50 kHz), and the weight, gender, height, age of person for which impedance is measured. The above-noted factors impact the resistance of the tissues themselves and the tissue reactance due to the capacitance of membranes, tissue interfaces and non-ionic tissues. The measured resistance may be considered to be approximately equivalent to the resistance of muscle tissue.

In an embodiment, physiological sensors 1110B-1110D each comprising a metallic contact may additionally or alternative be employed to monitor, based on measuring bio-potential, electrical body activity to obtain ECG, EMG and/or EEG signals. In order obtain ECG readings for example, physiological sensors 1110B-1110D can be brought into contact with Limbs for obtaining "limb leads" or "augmented limb leads". For example, a finger of one of the user's two hands may be in contact with the electrode of a first physiological sensor 1110B, while the finger of the user's other hand may be in contact with the electrode of a second physiological sensor 1110C, and a third finger of either one of the user's hands may be set to be in contact with the electrode of a third physiological sensor 1110D at the same time, for example, to generate contact in approximate accordance with the so-called "Eindhoven triangle" for obtaining ECG readings, e.g., for extracting heart rate and/or detecting cardiac arrhythmias including, for example, Tachycardia, Bradycardia, Pause and/or Atrial Fibrillation (AF). In some embodiments, heart rate variability parameter may be determined. In an embodiment, impedance measurement may be performed, for example, using two of physiological sensors 1110B-1110D in that the user concurrently engages a finger of his/her hand and a finger of her/her foot with respective different sensors 1110.

EMG signals may also be obtained via the electrodes of physiological sensors 1110B-1110D. For example, EMG signals of the user's flexor carpi muscle group between two fingers of one of his/her hands may be obtained when the user places the corresponding two neighboring fingers on the metallic pads of two of physiological sensors physiological sensors 1110B-1110D.

Figure 3:
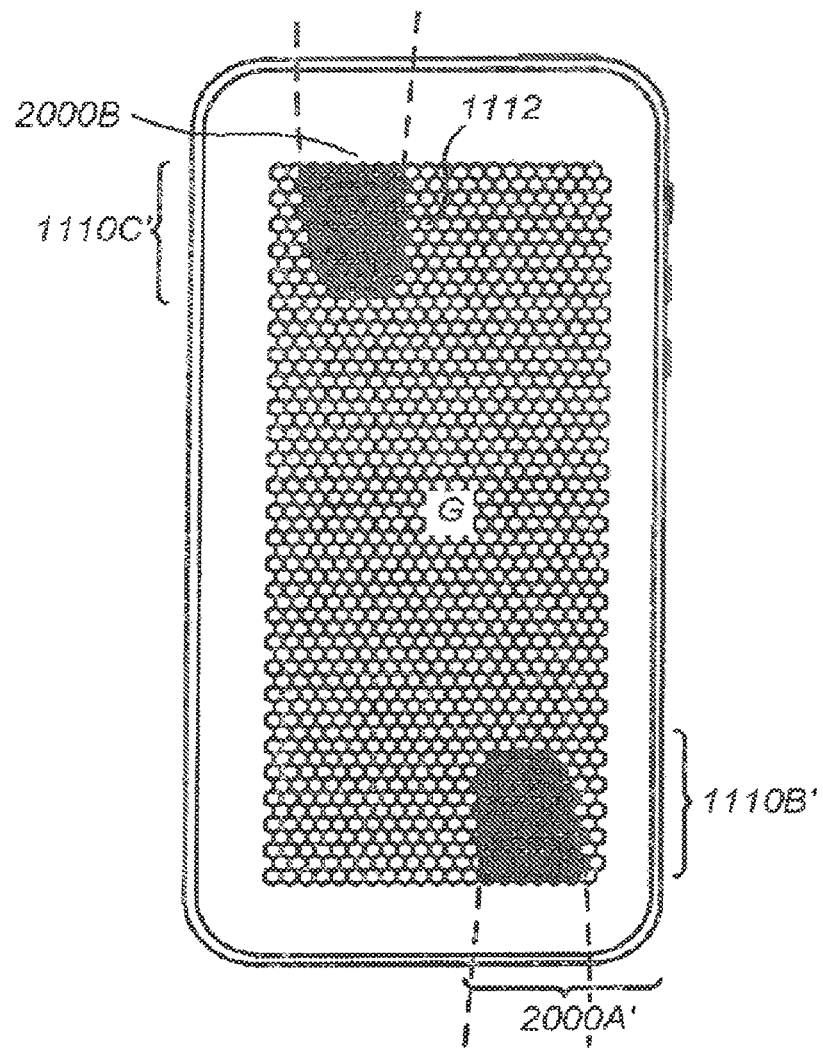
FIG. 3 is a schematic illustration of an exemplary sensor electrode array.

Additional reference is made to FIG. 3. In another embodiment, sensors 1110B'-1110D' may each be implemented as part of a sensor electrodes array (not shown). The sensor electrode array may for example comprise a plurality of individual conductive elements 1112 in a column-row "electrode-pixel" arrangement. Alternatively, the array of conductive elements 1112 may be arranged according to a pixel grid of hexagonal shaped conductive elements 1112. In either case, the electrode-pixels may each be electrically (e.g., galvanically) isolated from one another so that by simultaneously touching any two or three regions of the sensor electrode array by respective two or three different body portions (e.g., fingers 2000A and 2000B) of the same user, the pixel array may enable deriving information about body composition and/or its electrical activity. Each region may comprise a set of a plurality of conductive elements 1112. Hence, a first body portion and second body portion touching such sensor electrode array "creates" respective physiological sensors 1110B' and 1110C' (shaded conductive elements), wherein each such sensor comprises a plurality of electrodes of the sensor electrode array. Non-shaded elements are not engaged by the user's finger 2000A and 2000B. Conductive elements 1112 are operably coupled with a processor comprised in cover sensor assembly 1100 for continuously measuring conduction and control creation of different physiological sensors 1110B'-1110D'. Specific reference to a processor comprised in cover sensor assembly 1100 will be made with respect to FIG. 4.

In summary, the cover sensor assembly has an array of conductive elements integrated therein, each of the conductive elements being electrically isolated from other conductive elements, such that when a sub-group of the conductive elements are electrically coupled together (e.g. with a finger 2000A) the sub-group operates as a first physiological sensor 1110B'. The physiological data acquisition module is configured to generate data descriptive of a physical stimulus received by the first physiological sensor.

A second sub-group of conductive elements operate as a second physiological sensor 1110C' when the second sub-group of conductive sensors are electrically coupled together (e.g. with a finger 2000B) and the physiological data acquisition module is further adapted to generate data descriptive of physical stimuli received by the first physiological sensor 1110B' and the second physiological sensor 1110C'. Optionally, a third finger (not shown) can form a third sub-group which operates as a third physiological sensor 1110D'.

Validation Sensors:

As already briefly outlined herein, cover sensor assembly 1100 may comprise validation sensors 1120 for controlling the validity status of a physiological parameter measurement executed by physiological sensors 1110. For the everyday user who is not a medical professional, one of the biggest problems is the incorrect use of medical devices. For that reason, devices intended for domestic use need to be "idiot proof". The apparatus of the immediate system not only provides the physiological sensors integrated into a smartphone cover (jacket) but also includes validation sensors 1120 which are additional sensors to ensure that the user is placing his or her fingers in the correct position, applying the correct amount of pressure, that the fingers or hands are not sweaty etc. Non-limiting examples of such validation sensors 1120 may include a pressure sensor, a force sensor, a temperature sensor, an impedance sensor, a capacitance, a torque sensor, an accelerometer, a barometer, a light sensor and/or a humidity sensor.

Reverting to FIGS. 1B and 1C, photoplethysmograph sensor 1110A of cover sensor assembly 1100 may for example be employed in conjunction with a validation sensor embodied by a pressure sensor 1120A which may be located next to the photoplethysmograph sensor so that one area of the user's finger may operable engage with photoplethysmograph sensor 1110A for taking the SpO$_2$ measurement for example, while concurrently applying pressure on pressure sensor 1120A (e.g., in that another area of the same finger may concurrently engage with a pressure sensor or a pressure sensor is located beneath sensor 1110A so that placing a finger onto sensor 1110A causes the sensor to be pressed against the pressure sensor). In an embodiment, pressure sensor 1120A may be located beneath photoplethysmograph sensor. In either embodiment, it is assumed that the magnitude of the pressure applied by the finger onto photoplethysmograph sensor 1110A may be substantially the same as the pressure applied by the finger onto pressure sensor 1120A.

In an embodiment, the pressure that may be requested to be applied by the user may, for example, be positive ($P_{finger}$>0 mmHg) but less than the user's diastolic pressure (e.g., <30 mmHg or <60 mmHg). In an embodiment, the applied pressure may be 80% or less than a Gold Standard diastolic pressure.

In an embodiment, the cover sensor assembly 1100 with one or more validation sensors 1120 can be operably engaged with a computerized mobile device 1200. Monitoring system 1000 may be operative to enable the implementation of a monitoring method, process and/or operation by providing a visual aid for ensuring the correct positioning of the relevant body part in conjunction with the physiological sensor 1110. The validation sensor(s) 1120 provides sensor data such as pressure, light, temperature etc. which is processed and visually displayed on the display of the mobile device in an instructive manner. For example, an application on the mobile device displays a red to green scale with a pointer that indicates the right amount of pressure (e.g. when the pointer is in the green area) or the wrong amount of pressure (e.g. when the pointer is in the red area) so the user can see if he or she is applying the correct amount of pressure.

In an embodiment, in addition to ensuring that the pressure applied by a user's finger lies within a specified range, the position of a user's finger relative to the photoplethysmograph shall be substantially identical for repeated measurements to eliminate or reduce deviations in repeated measurements due to different positioning of a user's finger relative to the photoplethysmograph. In an embodiment, photoplethysmograph sensor 1110A may thus be employed in conjunction with a validation sensor embodied by a position sensor arrangement 1120B which is configured to sense the position and orientation of the body portion (e.g., a finger) that is brought into contact with photoplethysmograph sensor 1110A relative to the position sensor arrangement 1120B.

The operating principles of such position sensor arrangement 1120B may for example be based on measuring electrical parameters such as impedance and/or capacitance of a body. Each one of one or more position sensor arrangements 1120B may for example comprise a plurality of impedance or capacitance sensor elements 1120B surrounding or encircling a respective one or more physiological sensors 1110A-1110D and, optionally a corresponding validation sensor. For example, a plurality of sensor elements 1120B of a given position sensor arrangement 1120B may encircle physiological sensor 1110B. Measurement of impedance or capacitance by an "encircling" sensor element may be indicative of contact being made by human tissue with such sensor element. Conversely, not measuring impedance or capacitance may be indicative that human tissue does not make contact with such "encircling" sensor element. Accordingly, based on for example impedance and/or capacitance readings, information about the position of a user's body portion (e.g., finger) with respect to physiological sensor 1110B may be derived.

In an embodiment, photoplethysmograph sensor 1110A may be employed in conjunction with a validation sensor embodied by a temperature sensor (not shown), e.g., to correct for variations in oxygen saturations readings that may be influenced by the temperature of the tissue area that engages with photoplethysmograph sensor 1110A.

In an embodiment, photoplethysmograph sensor 1110A may be employed in conjunction with a validation sensor embodied by a light sensor (not shown), e.g., for sensing the amount of ambient light. For example, if the photoplethysmograph sensor 1110A is exposed to too much light, as sensed by the light sensor, then photoplethysmograph sensor 1110A will not take the reading. In some embodiments, an application running on the computerized mobile device 1200 operably engaged with the cover sensor assembly 1100, will display a notification and/or set of instructions for correctly positioning the applicable. For example, the user is instructed to reposition the finger over the photoplethysmograph sensor 1110A, which in turn properly covers the light sensor, so that no ambient light interferes with the measurement.

In an embodiment, sensors 1110B-1110D that are operative to measure electrical body activity to obtain ECG, EMG and/or EEG signals may for example be employed in conjunction with validation sensors that are embodied by conductance sensors to determine validity of the obtained ECG, EMG and/or EEG signals. Such conductance sensors may determine skin humidity, size of contact area between biological tissue and the electrode, and/or the magnitude of the pressure applied by the user's body portion (e.g., a finger) that is in contact with the electrode included in sensors 1110B-1110D.

Reverting to FIGS. 2A and 2B, monitoring engine 1500 may ensure correct positioning of a temperature sensor 1110F and 1110Fa relative to tissue of the body portion, e.g., by providing corresponding instructions to the user thereof.

In some embodiments, with respect to IR-based temperature sensor 1110F and 1110Fa, monitoring engine 1500 may be operative to determine whether tissue comprises sufficiently high density of blood cells to ensure reliable temperature measurement. During temperature measurement, the signal obtained indicative of the temperature is analyzed by monitoring engine 1500 to provide an accurate estimation of core temperature (while the skin temperature is being measured).

Temperature sensor 1110F and 1110Fa may be employed in conjunction with a temperature validation sensor 1120F and 111Fa to ensure that the positioning requirements of IR- or contact-based temperature sensor 1110F and 1110Fa and the tissue area based on which the body or skin temperature is measured are met.

Temperature validation sensor 1120F may for example be embodied by a Galvanic Skin Response (GSR) sensor that works together with an IR temperature sensor to ensure that the finger or hand is not wet or sweaty, both of which can cause the IR sensor to return a wrong measurement.

Temperature validation sensor 1120F may, for example, be embodied by a contact sensor and/or a proximity sensor. The operating principles of such contact sensor may, for example, be based on electrical parameters such as determining impedance and/or capacitance between electrical contacts (not shown). In yet another example, proximity sensors can measure the angle of the finger (or other body part) in frictional engagement with the IR sensor to ensure that the finger is flat on the sensor and not at an angle (which would skew the temperature reading).

Figure 9A:
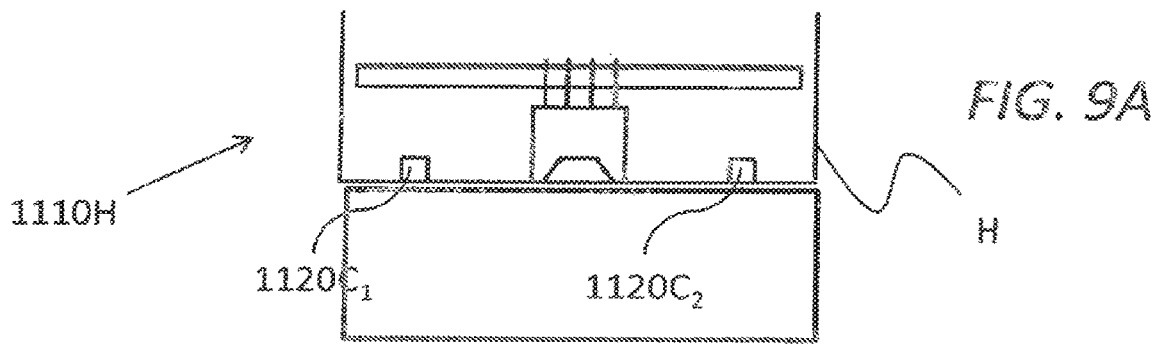
FIG. 9A-9C show embodiments of an exemplary temperature sensor.
Figure 9B:
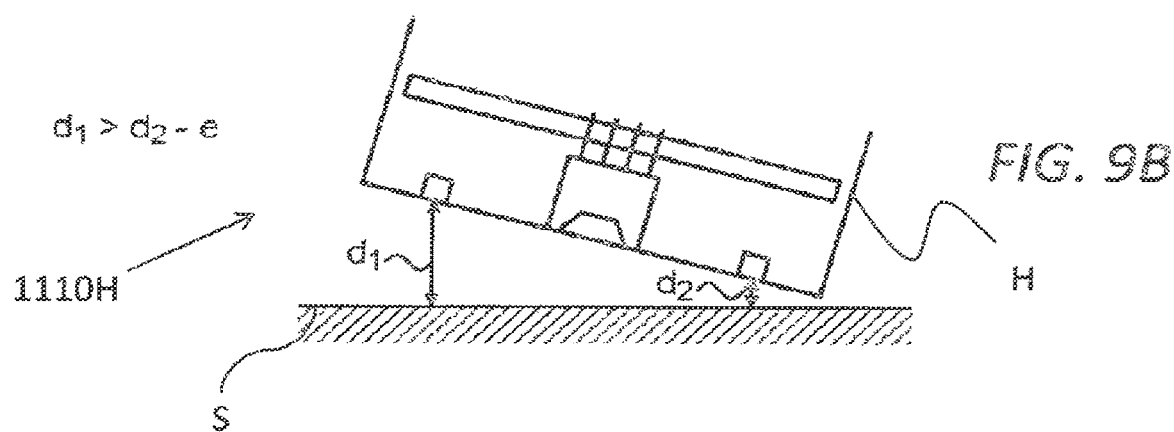
Figure 9C:
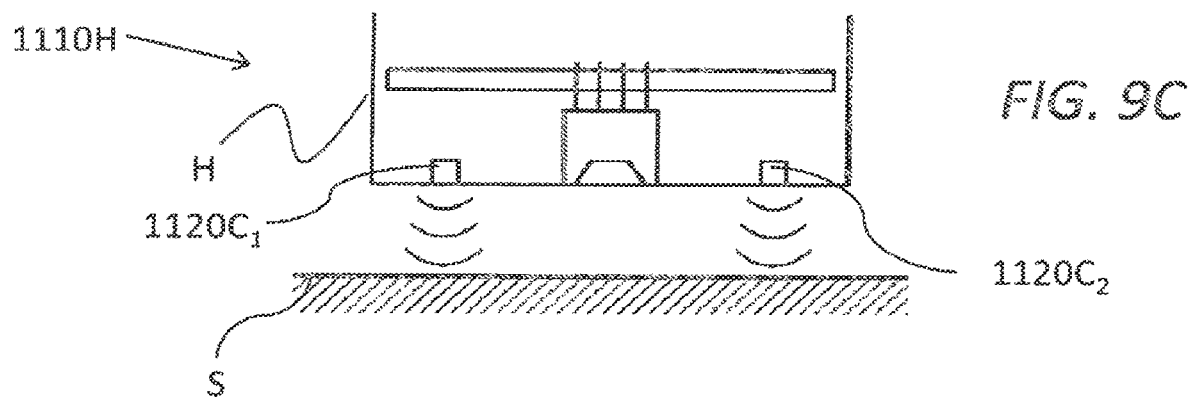

Reference is now made briefly to FIGS. 9A-C. FIG. 9A is an exemplary temperature sensor 1110H that may be integrated into cover sensor assembly 1100. The temperature sensor 1110H, in an exemplarily embodiment, is housed in a housing H that includes an IR sensor 1110H for sensing a body temperature as discussed above. In addition to the IR sensor 1110H, housing H further includes two proximity sensors 1120C which are located, for example, one on each side of the IR sensor. The proximity sensors act as validity sensors that ensure that the desired body part (e.g. finger) is positioned flush (flat) against the IR sensor 1110I and not at an angle.

Each of the proximity sensors 1120C measures the distance between the sensor and the sensed surface. In FIG. 9B, the housing of the temperature sensor 1110H is erroneously set at an angle with the target surface as opposed to being flush (flat) against the surface. If the temperature reading is taken when the IR sensor is the depicted angle, the sensor reading will not properly reflect the physiological data of the user. Proximity sensor one $1120C_1$ measures a distance d1 between the sensor and the surface. Proximity sensor two $1120C_2$ measures a distance d2 between the sensor and the surface. If d1 is greater or smaller than d2, by at least a predetermined amount, the processor in the cover sensor assembly is able to determine that the IR sensor 1110H is not totally flat or sufficiently flat against the target surface, as desired. In one embodiment, the device will not take a reading in such a situation. In another embodiment, the device with additionally or alternatively provide a notification that the device is not correctly positioned.

FIG. 9C illustrates the temperature sensor 1110H of FIGS. 9A and 9B perpendicular to a surface S, but spaced apart from that surface. Proximity sensors one $1120C_1$ and two $1120C_2$ each provide a proximity sensor reading corresponding to the distance between the respective proximity sensor and the surface. If the sensor values are equal to each other then the device is determined to be at the appropriate angle. If the sensor values are within a predetermined range, then the sensor is close enough to the target surface S to receive the desired reading. Potentially, the target surface S may be uneven, even to a slight degree. As such, when the processor 1130 compares the sensor readings of proximity sensor one $1120C_1$ with the readings of proximity sensor two $1120C_2$, the processor allows for a slight, predetermined discrepancy between the sensor data values.

Prior to a first use, temperature sensors 1110F and 1110Fa may be calibrated per user for human skin emission and per body portion (e.g., oral temperature or blood temperature). The calibration will have to be done during a clinical study that should include subjects with body temperature value that shall cover substantially all the physiological body temperature range.

In an embodiment, monitoring system 1000 may be configured to process only data descriptive of values received from physiological sensors 1110 (e.g., photoplethysmograph sensor 1110A, bio-potential measurement sensors 1110B-1110D) for which it is determined, based on the validation sensor(s), that the values of the physiological parameters is valid. In an embodiment, system 1000 may provide an output to the user which is indicative of whether the determined value(s) is/are valid or not. Optionally, the output may indicate the user that measurements have to be repeated. Preferably, the output is indicated on a display of the computerized mobile device 1200 operably engaged with the cover assembly 1100 as discussed above. Alternatively or additionally, cover assembly 110 may include one or more LEDs configured to indicate whether the reading was successful/valid (e.g. a green LED lighting up) or not successful/valid (e.g. a red LED lighting up).

In an embodiment, the values for a plurality of different parameters may be determined from a single sensor position. For instance, photoplethysmograph 1110A may be employed for the measurement of a heart rate, peripheral oxygen saturation, and/or systolic pressure. In an embodiment, heart rate values measured from photoplethysmograph 1110A may be compared with heart rate values derived from ECG waveforms. In an embodiment, depending on a determined degree of validity, heart rate measured from photoplethysmograph 1110A may be displayed to the user, or heart rate derived from ECG signals may be displayed to the user. In an embodiment, depending on a determined degree of validity, different weightings may be assigned to heart rate derived from photoplethysmograph 1110A and to heart rate derived from ECG signals to obtain the most reliable results.

In an embodiment, one or more hardware components may be shared by a physiological sensor and a validation sensor. For instance, electrodes of sensors 1110A and 1110B may be employed for bioimpedance measurements and, at the same time, for determining conductance between the body portions that are in engagement with physiological sensors 1110A and 1110B for determining whether the contact made meets the requirements that ensure valid determination of physical parameters values.

Stress Indication:

In an embodiment, system 1000 may be operative to provide the user with an indication of his/her stress level, which may herein be referred to as a stress indicator value (SI). The SI value may be obtained, for example, by determining the instantaneous values for a plurality of physiological parameters, during a monitored time period (e.g., 30 seconds) having the same monitoring start time stamp (e.g., 11:00 AM). Physiological parameters values that may be determined for deriving the SI value of a user may include, for example, bioimpedance, skin temperature, heart rate and/or a user's cardiac activity parameters represented by an ECG signal over a period of time. The determined physiological parameter values may be fused to obtain a value which may be indicative of the user's level of stress during the said monitoring time period. As used herein, "fusion" may be exemplarily performed by a supervised machine learning algorithm in order to find the relation between two or more measured or calculated parameter(s) and stress response.

In an embodiment, a biofeedback procedure may be carried out in order to determine a user's SI value. The biofeedback procedure may include subjecting the user to a stimulating or, conversely, soothing input aimed at exciting or relaxing the user, respectively. Such input may herein also be referred to as "biofeedback input". The user's individual response to the biofeedback input may be determined, e.g., by determining a variation in the value of one or more physiological parameters. A variation may be determined by measuring the magnitude in drop or increase of a physiological parameter value. Based on a measured variation in the physiological values responsive to such biofeedback input, the user's SI value may be determined.

In an embodiment, a variation in a physiological parameter value responsive to a biofeedback input may be compared against a variation in a physiological parameter value of other users that were subjected to the same biofeedback input and/or against a variation in a physiological parameter value of the same user in different test occasions. A soothing biofeedback input may for example include a series of images, a video and/or audio considered to have a relaxing effect on humans. Conversely, a stimulating biofeedback input may include a serious of images, a video and/or audio considered to have an exciting effect on humans.

In an embodiment, data descriptive of the responses of a user to biofeedback inputs may be accumulated to obtain or "learn" a personalized stress-response profile of the user. The user's stress-response profile may serve as a basis or reference for determining the user's SI value.

For example: the user may several times (e.g., sequentially) be exposed to a biofeedback test comprising subjecting the user to a plurality of stimuli which are each supposed to calm the user. Such calm-inducing stimuli may comprise calming music, relaxation exercise instructions (e.g., breathing slowly). In addition, after completing subjecting the calming-stimuli, the user may be subjected to stimuli that are supposed to increase the user's stress level. Such stress-inducing stimuli may comprise challenging the user with an unsolvable mathematical problem. The user's physiological response may then be classified or grouped according to whether the biofeedback test included subjecting the user to calming or stress-inducing stimuli to obtain two sets of data descriptive of the user's response to such calm-inducing and stress-inducing stimuli, respectively. Based on the two sets of data, a stimuli-response or biofeedback profile of the user may be derived. A stress "spot" measurement can be indicative of the user's stress level with reference to the user's stimuli-response or biofeedback profile.

In an embodiment, data descriptive of the individual responses of a plurality of users' responses to biofeedback inputs may be accumulated to obtain or "learn" a personalized stress-response profile for each one of the plurality of users. The personalized stress-responsive profiles of a respective plurality of users may serve as a basis for determining a stress-response profile norm (e.g., expressed by normalized Gaussian distributions in variations respective of physiological parameter values). A user's individual response (e.g., stress profile) may be compared against the normalized stress-response profile for determining the user's SI value.

In an embodiment, a user's response to calm- and stress-inducing stimuli may be acquired via a microphone (not shown) comprised in cover sensor assembly 1100 and/or mobile device 1200. For example, an utterance of the user may be received by such microphone and converted into electrical or optical signals descriptive of the utterance. These utterance-related signals may then be processed by monitoring engine 1500 to determine a value related to the utterance, wherein the value is descriptive of a psychological stress level of the user.

In an embodiment, monitoring system 1000 may be operative to function as a lie detector. For example, based on measured physiological parameters like, e.g., heart rate, skin conductivity, photoplethysmograph signal amplitude and the like, monitoring engine 1500 may determine a score which may be indicative of the likelihood that an individual being examined is lying or not. For instance, increased skin conductivity may be indicative of excessive sweating which, in turn, may be considered as an indication that the individual is lying. Analogously, a comparably increased heart rate may as well provide an indication that the individual is lying. Conversely, unsubstantial changes or decrease heart rate and/or skin conductivity may be indicative that the individual is truthful.

In an embodiment, measured physiological parameters like, e.g., body temperature, optionally in combination with heart rate, may provide an indication about the likelihood of ovulation in a female user.

Electrical Isolation Between Mobile Device and Sensors During Charging:

Reference is now made to FIGS. 6A-6C. According to an embodiment, monitoring system 1000 may be configured so that while an internal power unit (not shown) of mobile device 1200 is charged by an external power supply (not shown), sensor assembly 1100 is electrically isolated from the external power supply to avoid electrocution of a user who might accidentally or intentionally touch an electrode of sensor assembly 1100. For example, when in an operable configuration that allows determining physiological parameter values, i.e., monitoring system 1000 is in "an operating mode", an electrical switch (not shown) of monitoring system 1000 is in a first position, providing electrical contact between the sensors of cover sensor assembly 1100 and the internal power unit (not shown) of mobile device 1200. In this way, the internal power unit may for example power the components of mobile device 1200 as well as components of cover sensor assembly 1100.

However, when mobile device 1200 is electrically connected to an external power supply, the switch may, in an embodiment, be set by the power supply cable (not shown) into another, "disconnected", position. The switch thus acts as a "disconnector". In the other position, the electrical components of mobile device 1200 (the internal power unit) may be disconnected and hence electrically isolated from the electrical components of cover sensor assembly 1100. Therefore, during the charging of internal power unit of mobile device 1200 by the external power supply, physiological sensors 1110 may be electrically isolated from the external power supply (not shown). In disconnected state, the switch may provide electrical isolation of up to 4000 Volt for example. In an embodiment, the switch or connector may be comprised in cover sensor assembly 1100.

Exemplarily, the disconnection operation referred to above may be performed by a disconnector 3000, shown in FIGS. 6A-6C. Disconnector 3000 is operable to provide electrical isolation between PCB contacts row 'A' (3000e) and row 'B' (3000d). When the disconnector is in an extended position (as in FIG. 5B), contacts 3000e are electrically connected to contacts 3000d through flexible contacts 3000s. When an electric plug (of a power line for example) is inserted and pushes a "fork" or trowel 3000c, flexible contacts 3000a which are held in a chassis 3000b are lifted and disconnected from contacts 3000d.

For example, a disconnector such as disconnector 3000 can be used instead of large isolation components (such as optocouplers) in a medical application where an isolation of 4 kV is needed between a power line and any device in physical contact with a human body.

In an embodiment, the electrical current required to operate the electronic components of cover sensor assembly 1100 may for example be 30 mA or less. In an embodiment, as indicated herein, the electrical current for powering the electronic components of cover sensor assembly 1100 may be fed from power module 1180 of cover sensor assembly 1100 and/or power module 1280 of mobile device 1200.

An alternative embodiment is depicted in FIGS. 6D-6G. In the depicted embodiment, the switch or connector (referred to herein as coupler 3100) may be comprised in cover sensor assembly 1100. In most handheld mobile devices today, the power port is also the data port. The power cord can either be plugged into a dedicated energy source such as a wall socket or into a combination energy and data source, such as a desktop or laptop computer where the handheld device draws power from the mains or battery of the larger computing device and can also communicate data between the devices.

As such, a connector or switch for a dual purpose input/output (I/O) port must be capable of disconnecting the sensors from the energy source while at the same time allowing the data connectors to remain coupled.

Figure 8A:
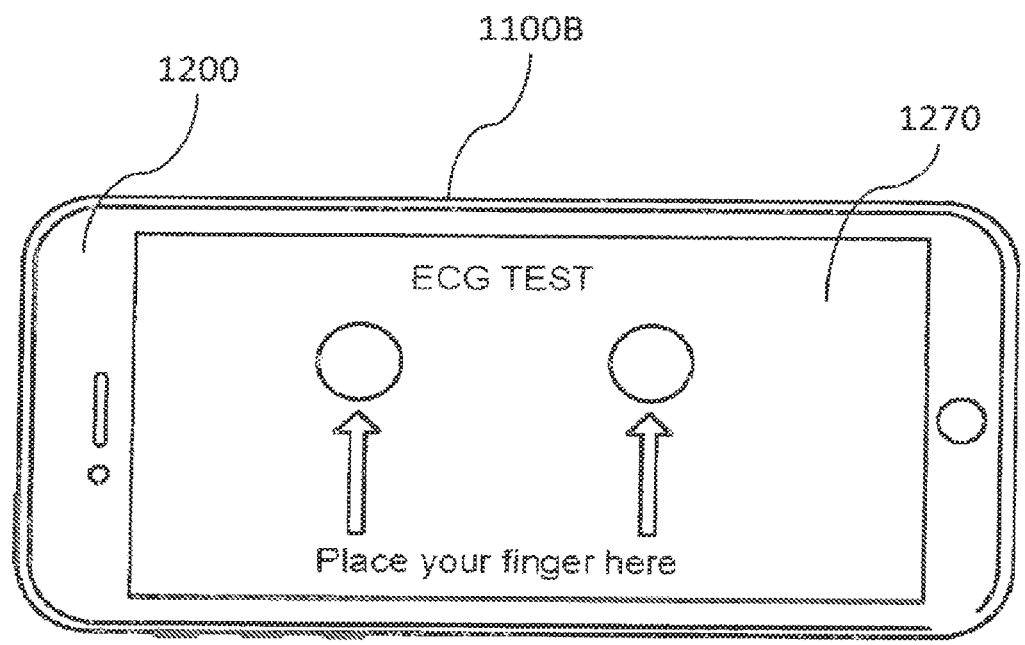
FIG. 8A-C show embodiments of the cover assembly coupled to a mobile computing device with a capacitive touch screen.
Figure 8B:
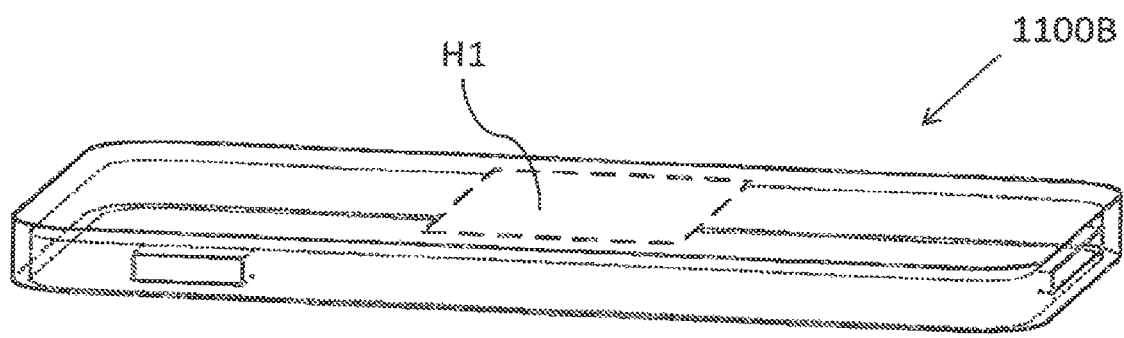
Figure 8C:
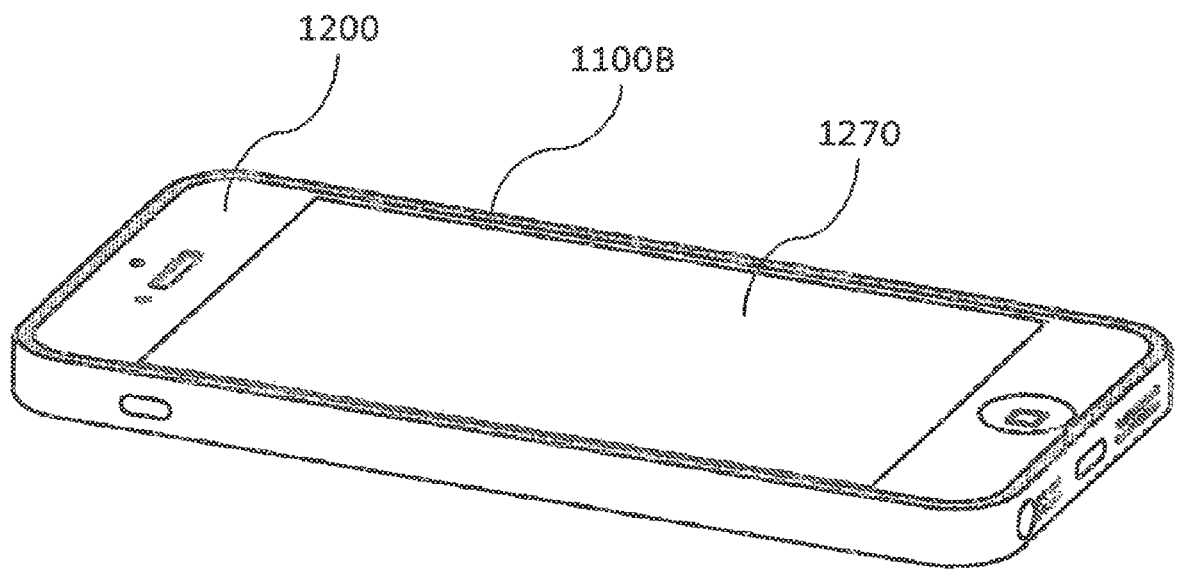

In one exemplary embodiment, the cover assembly includes an I/O coupler 3100 that connects to, or otherwise makes electrical contact with a power/data port of the computerized mobile device (e.g. the I/O port of mobile device 1200 depicted in FIG. 8C). Two common examples of computerized mobile devices are smartphones such as an iPhone® and a Samsung® device running an Android™ operating system. The iPhone includes a dock connector or Apple Lightning® connector port while most current Samsung smartphones have a micro-USB port.

In one exemplary embodiment, cover assembly 1100 includes an adaptor which is adapted to electrically couple the cover assembly 1100 to computerized mobile device 1200 via the I/O port. The adaptor (e.g. coupler 3100) may be a male connector (plug) that enters the female port (socket) of computerized mobile device 1200. Cover assembly 1100 can draw power from the battery of computerized mobile device 1200 as well as being in electronic data communication with the device.

In the same or other embodiment, the adaptor [further] has a female connector (socket) on the external side of the cover assembly 1100. The female connector serves as an extension port for the integral mobile device I/O port and provides the same data and power functionalities to computerized mobile device 1200 as the mobile device's I/O port. A power/data cable is inserted into the socket end of the adaptor and facilitates both power and data connectivity to the computerized mobile device 1200. Innovatively coupler 3100 servers as a power switch or "decoupler" between the power/data cable and cover assembly 1100.

Figure 6D:
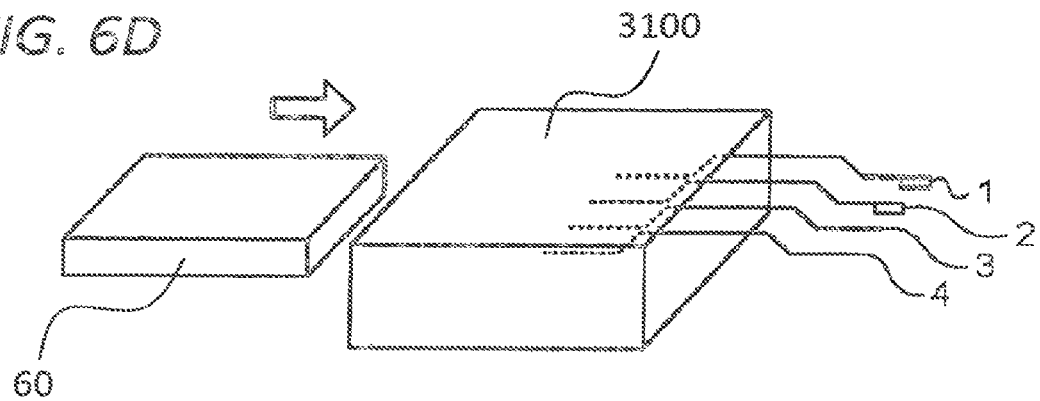
FIG. 6D-G show other switch/disconnecting mechanisms.
Figure 6E:
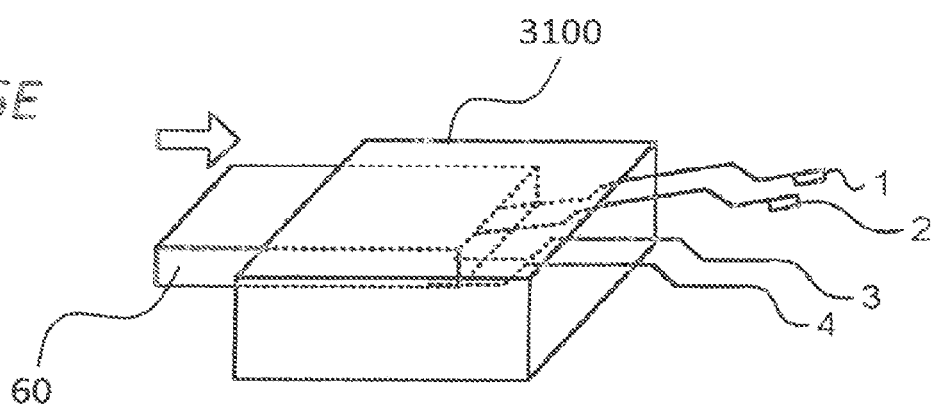

As shown in FIG. 6D, a connector head 60 is coupled to a power/data cord (not shown). The connector head 60 is depicted proximal to coupler 3100. In FIG. 6E, connector head 60 enters into the female, socket side of coupler 3100 and comes into contact with connector pins 1-4. Connector pins 1-4 are merely an exemplary arrangement of connectors that include both data and power connectors. Exemplarily, connector pins 1-4 are compatible with a Universal Serial Bus (USB) connector that also has four connector pins. Many different types of connectors and adaptors exist, but generally all the dual power and data connectors have one power pin, at least two data pins and a ground pin. Exemplarily, pin 1 of coupler 3100 is a power pin. Pin 2 is the ground (GND) pin. Pin 3 is a data plus (D+) pin and Pin 4 is a data minus (D−) data pin.

Coupler 3100 has a "coupled state" and a "de-coupled state". In the coupled state, cover assembly 1100 is in electrical communication with computerized mobile device 1200 via both the power pins and the data pins. The coupler is depicted in the coupled state in FIG. 6D. In FIG. 6E, coupler 3100 is in the de-coupled state whereby power pins 1 and 2 are in a raised position and data pins 3 and 4 are in the straight, coupled position.

Figure 6F:
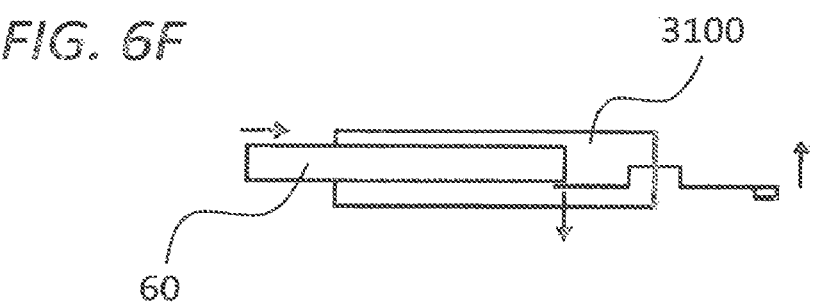
Figure 6G:
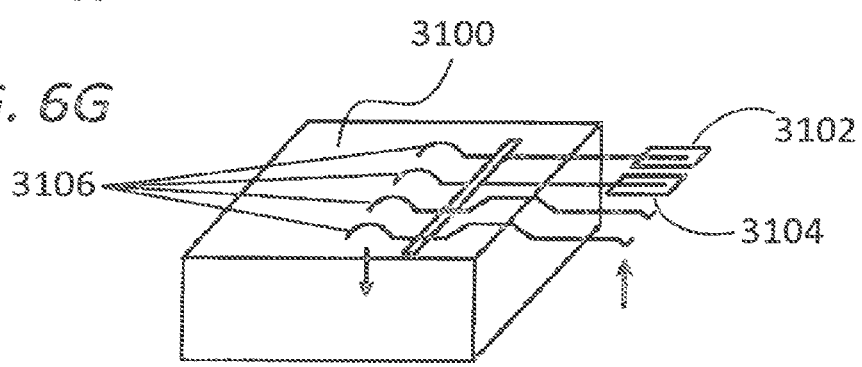

Power pins 1 and 2 (live and ground) are flexible and moveable. The pins are set on a rotatable axis that is biased to the coupled position so that when the power cable is not connected, the cover assembly is able to draw power from the mobile computing device as well as communicate data between the two devices. In FIG. 6E power/data cable head 60 is inserted into the socket end of coupler 3100 and mechanically biases the power pins to the raised (de-coupled) position. In the raised position, the power pins couple the power cable to the computerized mobile device 1200 while de-coupling the power cable from cover assembly 1100. FIG. 6F depicts the interaction between coupler 3100 and power/data cable head 60 with directing arrows indicating the various directions in which the components move. Head 60 is inserted into coupler 3100. The front edge of the cable forces the back edge of the connecting pin down such that the front end of the pin rises (as shown in FIG. 6E). Pins 3 and 4 are soldered in place and do not rise up. FIG. 6G depicts an alternative embodiment wherein pins 1 and 2 are soldered to solder pads 3102 and 3104 and pins 3 and 4 are moveable. In the depicted configuration, the back ends of the pins include displaceable humps 3106 which are adapted to be depressed when head 60 is inserted into coupler 3100.

Multiple Types of Analyses for Single Blood Strip

A "blood-composition" sensor 1110G operative to determine the blood type sampled by a strip 1111. The Monitoring system is operative to enable, among other functions, transmission of blood-related information including, for e.g., glucose level, cholesterol level and/or blood type to a third party. The innovative Monitoring System can determine both glucose and cholesterol level from a single test strip via the same interface, such that by engaging the test strip only once with the sensor, the user obtains readings both for his/her glucose and LDL cholesterol levels. As used herein, the glucose test is used as an exemplary blood test that is representative of all the types of blood strip tests that function by using amperometry. As used herein, the cholesterol blood strip test is used as an exemplary blood strip test that functions by using optical components to analyze the blood sample on the test strip. Therefore, the use of a glucose strip test herein is intended to relate to all blood strip tests that use amperometry and a cholesterol blood strip test as used herein, is intended to relate to all blood strip tests that employ optical analysis of the blood sample on the strip.

The immediate device can read glucose strips, cholesterol strips and innovative, combination strips for both glucose and cholesterol. The monitoring engine is able to determine the type of test strip engaged with physiological sensor (glucose, cholesterol or combination test strip) and provide a corresponding output.

The sensor used for glucose measurement can be based on conversion of glucose concentration into a voltage or current signal. Accordingly, the strips are operative to allow amperometry. In an embodiment, the part of sensor for glucose measurement can comprise a platinum and silver electrode forming part of an electric circuit where hydrogen peroxide is electrolyzed. The hydrogen peroxide is produced as a result of the oxidation of glucose on a glucose oxide membrane. The current through the circuit provides a measurement of the concentration of hydrogen peroxide which, in turn, provides an indication of the glucose concentration on the blood sample of the test strip.

Cholesterol test results are based on the Meter reading light reflected off a test strip that has changed color after blood has been places on the strip. The deeper the color is, the higher the cholesterol level. The Meter converts this reading into a Cholesterol result and displays it.

Individual glucose monitors and cholesterol monitors are both known in the art. A multi-test monitor device, as disclosed herein, which includes both the glucose and cholesterol testing capabilities, is not known in the art. The immediate applications discloses a multi-test monitoring device that is capable of measuring a first measurement (e.g. a glucose test), a second measurement (e.g. a cholesterol test) or a both a first and a second measurement in a single device from a single strip. The type of measurement performed by the device is dependent on the type of strip (e.g. a glucose strip, a cholesterol strip or glucose and cholesterol strip) inserted in the monitoring device.

A multi-functional blood test strip monitor obviates the need for multiple monitors, as is the case to date. A Glucose monitor cannot simply be used as a cholesterol monitor by changing the type of test strip, as the two types of tests use different electronic components. The Glucose test uses amperometry and the cholesterol test uses a light source and optical element (e.g. photodetector). The innovative mechanism incorporated into the device cover includes both sets of components and an electronic or mechanical mechanism for differentiating between the different types of strips.

Capacitive Electrode Regions

Figure 7:
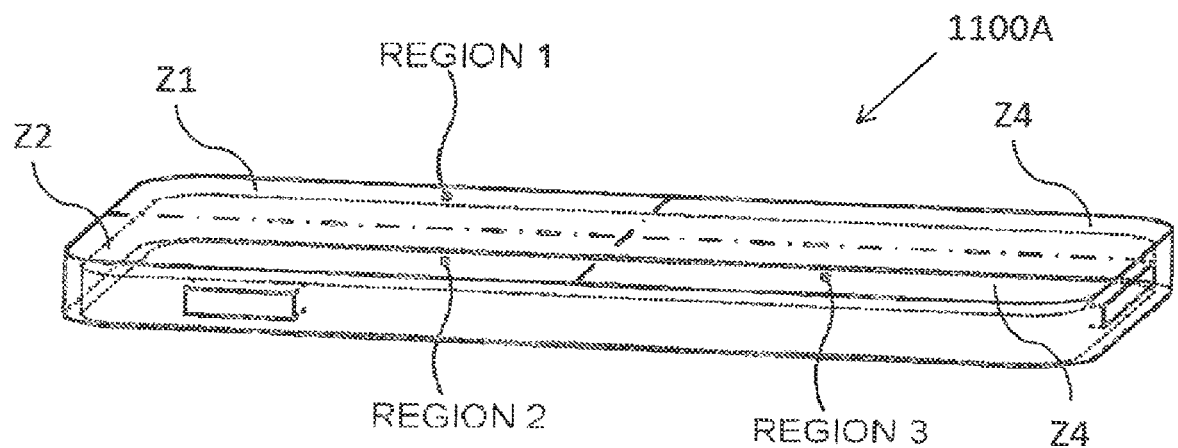
FIG. 7 is a diagram of an embodiment of the cover assembly including capacitance sensors.

Reference is now made to FIG. 7. FIG. 7 is a diagram of an embodiment of the cover assembly including capacitance sensors. According to an embodiment, monitoring system 1000 may comprise a cover sensor assembly 1100A which includes physiological sensors 1110I-K that are integrated into the backside of cover 1105. Cover sensor assembly 1100A is adapted to provide an electro-physiological monitoring function for, among other things, stress, body fat, heart rate, ECG etc. In preferred embodiments of the invention the cover sensor assembly 1100A includes physiological sensors 1110 that may be embodied by capacitive coupled sensors 1110I-K as opposed to resistive contact electrodes which are also known as (among other names) galvanic skin response (GSR) electrodes that are in galvanic contact with the user's body (see FIG. 1B). Cover sensor assembly 1100A of the immediate innovation includes two, three or four separate sensor regions Z1-Z4 for the user to place a finger on each of the regions. The sensors measure capacitance and derive various physiological parameters (HR, ECG, etc.) from the measurements.

Capacitance sensors are preferable over galvanic sensors as capacitance sensors do not need to be in direct contact with the skin of the user. As such, the high impedance of the skin does not affect the sensors' measurements as there is no need for direct contact with the skin. Furthermore, capacitance sensors are less sensitive to body motion at the monitoring area and muscle movement, both of which insert extraneous "noise" into the signals measured with galvanic electrodes.

The sensor network also overcomes further problems such as pressure. If a user provides too much pressure on a galvanic sensor, the signal is distorted and unwanted "noise" enters the signal. The signal captured by capacitive coupled sensors is not distorted by pressure.

Galvanic electrodes are unsightly as they are made from metallic, biocompatible materials. Heavy metals are not permissible and silver blackens over time. On the other hand, capacitive sensors do not need to be visible at all so that the cover can be regular plastic, covering over the electrodes.

Capacitive electrodes have been used for reading vital signs such as ECG, HR etc. Use of such electrodes in mobile device covers which are attached to the mobile device and in communication with the device, are not known. Regions Z1-Z4 provide large areas for the user to place his or her fingers without the need to take special care with the exact placement of the fingers (as is the case with galvanic electrodes). This helps the product to be "idiot proof".

In an embodiment, Region 1 Z1 and Region 2 Z2 include capacitive electrodes 1110I and 1110J which are installed under backside of plastic cover 1105. In an embodiment, cover sensor assembly 1100A includes Regions 1-3 Z1-Z3. Each of the regions has one of capacitive electrodes 1110I, 1110J or 1110K installed there-under. In an embodiment, the Regions are demarcated on the plastic, silicone or rubberized cover 1105. In a similar manner to method described above with reference to FIGS. 1B-1C, for example, a finger of one of the user's two hands may be in contact with the Region 1 Z1, while the finger of the user's other hand may be in contact with Region 2 Z2, and—in embodiments with a third region—a third finger of either one of the user's hands may be set to be in contact with Region 3 Z3 at the same time, for example, to generate contact in approximate accordance with the so-called "Eindhoven triangle" for obtaining ECG readings, e.g., for extracting heart rate and/or detecting cardiac arrhythmias including, for example, Tachycardia, Bradycardia, Pause and/or Atrial Fibrillation (AF). In some embodiments, heart rate variability parameter may be determined.

Capacitive Electrode Zones on a Touch Screen

Referring to FIGS. 8A-8C, an exemplary embodiment of a monitoring system 1000 for monitoring physiological parameters may include a cover assembly 1100B that can be operably engaged with a computerized mobile device 1200. Computerized mobile device 1200 includes a touch-screen display and/or touch screen input area user interface 1270 that includes a capacitive touch screen. In preferred embodiments, the capacitive touch screen of the mobile device is operable coupled to the cover assembly via a wired connection.

FIG. 8B illustrates an isometric view of the back panel of the cover assembly 1100B. Cover assembly 1800 includes hardware and/or software encased in a housing H1 which is built into or operationally coupled to the inner surface of the cover assembly. The housing H1 of the cover assembly is depicted in phantom lines, as it is not readily visible from the depicted angle.

FIG. 8C illustrates an isometric view of a computerized mobile device 1200, including a capacitive touch screen user interface 1270, encased in cover assembly 1100B and operationally engaged therewith. Cover assembly 1100B uses the capacitive touch screen 1270 of the mobile device to sense physiological signals. Cover assembly 1100B includes a processor 1130, memory 1140, assembly monitoring engine 1150 communication module 1160 and, in some embodiments, a power module 1180. Most or all of the aforementioned components are housed in housing H1. Touch screen 1270 of the mobile device 1200 is used to provide capacitive coupled electrodes. Exemplarily, a software application is installed on computerized mobile device 1200. The application includes code stored in memory 1240 for computer-readable instructions that instruct the processor 1230 to display a user guide for placing the desired body parts in the desired positions on the capacitive touch screen 1270.

FIG. 8A illustrates an exemplary embodiment of system 1000 utilizing the capacitive touch screen for sensing physiological parameters. Exemplarily, the touch screen display 1270 shows two equal circles, spaced apart on the screen with the helpful instructions and arrows indicating that the user place his or her fingers on the circles. In some embodiments (not shown), the user is instructed to place a third finger on a third circle (not shown).

In other embodiments, the user is instructed to place a third finger on a physiological sensor integrated in cover assembly 1100B. Exemplarily, the third sensor may be integrated in the back panel of the cover assembly, in a similar manner to that which was discussed for cover assembly 1100A. Alternatively, the third sensor may be integrated into a corner of the cover assembly 1100B in a similar manner to sensor $1110B_2$ discussed above with reference to FIG. 1C, or integrated in a sidewall body portion of cover 1105.

Preferably, the user places a finger from each hand on one of the circles to receive a desired reading as discussed elsewhere. In some embodiments, use of a third finger, from either of the two hands, is employed to generate contact in approximate accordance with the so-called "Eindhoven triangle" for obtaining ECG readings which is discussed above.

Figure 4:
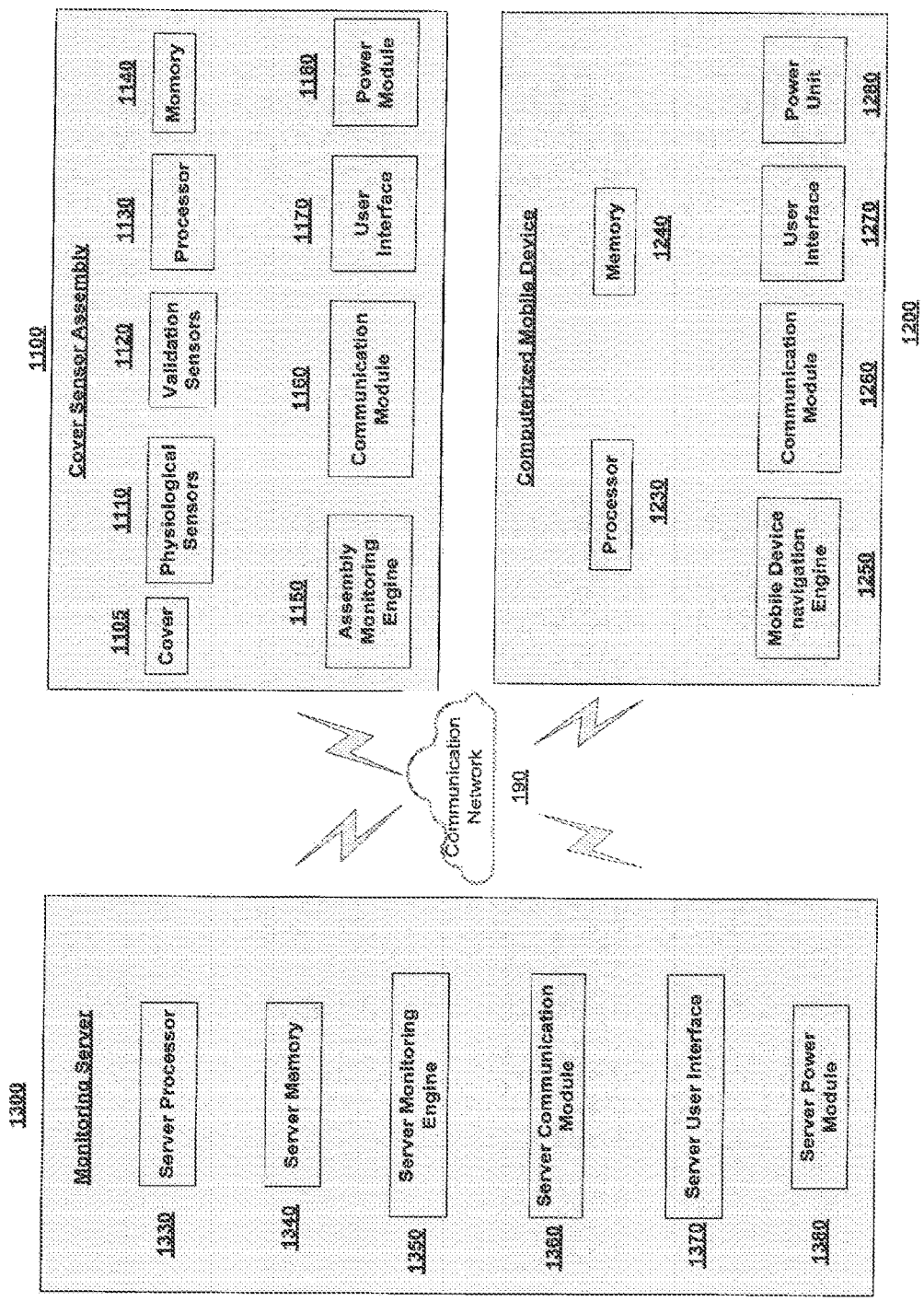
FIG. 4 is a schematic block diagram illustration of an embodiment of the system.

Additional reference is made to FIG. 4. Cover sensor assembly 1100 may include, in some embodiments, in addition to cover 1105, a physiological and/or a validation sensor 1110 and/or 1120, also a processor 1130; a sensor assembly memory 1140, a sensor assembly communication module 1160, a sensor assembly user interface 1170, and sensor assembly a power module 1180 for powering the various components of cover sensor assembly 1100. Computerized mobile device 1200 may include a processor 1230, a memory 1240, a mobile device communication module 1260, a mobile device user interface 1270, and a mobile device power module 1280 for powering the various components of computerized mobile device 1200.

In some embodiments, mobile device power module 1280 may power components of cover sensor assembly 1100 in which case, for example, cover sensor assembly may not employ power module 1180. In some other embodiments, sensor assembly power module 1180 may power components of computerized mobile device 1200.

Monitoring system 1000 may further include a monitoring server 1300, which may include a server processor 1330, a server memory 1340, a server communication module 1360, a server user interface 1370, and a server power module 1380, for powering the various components of monitoring server 1300. Monitoring server 1300 may for example relate to one or more servers, storage systems, cloud-based systems and/or services.

The various components of cover sensor assembly 1100, computerized mobile device 1200 and monitoring server 1300 may communicate with each other over one or more communication buses (not shown) and/or signal lines (not shown). Cover sensor assembly 1100 and computerized mobile device 1200 may communicate with monitoring server 1300 over a communication network 190 (schematically shown in FIG. 3).

The term "processor" as used herein may additionally or alternatively refer to a controller. Such processor may relate to various types of processors and/or processor architectures including, for example, embedded processors, communication processors, graphics processing unit (GPU)-accelerated computing, soft-core processors and/or embedded processors.

According to some embodiments, assembly memory 1140, mobile device memory 1240 and server memory 1340 may include one or more types of computer-readable storage media. Assembly memory 1140, mobile device memory 1240 and server memory 1340 may include transactional memory and/or long-term storage memory facilities and may function as file storage, document storage, program storage, or as a working memory. The latter may for example be in the form of a static random access memory (SRAM), dynamic random access memory (DRAM), read-only memory (ROM), cache or flash memory. As working memory assembly memory 1140, mobile device memory 1240 and/or server memory 1340 may, for example, process temporally-based instructions. As long-term memory, assembly memory 1140, mobile device memory 1240 and/or server memory 1340 may for example include a volatile or non-volatile computer storage medium, a hard disk drive, a solid state drive, a magnetic storage medium, a flash memory and/or other storage facility. A hardware memory facility may for example store a fixed information set (e.g., software code) including, but not limited to, a file, program, application, source code, object code, and the like.

Assembly communication module 1160, mobile device communication module 1260 and Server communication module 1360 may for example include I/O device drivers (not shown) and network interface drivers (not shown) for enabling the transmission and/or reception of signals carrying data over network 190. A device driver may for example, interface with a keypad or to a USB port. A network interface driver may for example execute protocols for the Internet, or an Intranet, Wide Area Network (WAN), Local Area Network (LAN) employing, e.g., Wireless Local Area Network (WLAN)), Metropolitan Area Network (MAN), Personal Area Network (PAN), extranet, 2G, 3G, 3.5G, 4G including for example Mobile WIMAX or Long Term Evolution (LTE) advanced, and/or any other current or future communication network, standard, and/or system.

Memory assembly memory 1140, mobile device memory 1240 and/or server memory 1340 may include instruction which, when executed, for example, by the respective sensor assembly processor 1130 and/or mobile device processor 1230 and/or server processor 1330, may cause the execution of the method, process and/or operation for monitoring physiological parameters of a user. Such method, process and/or operation may herein be implemented by monitoring engine 1500, e.g., as outlined herein above. According to some embodiments, some implementations and/or portions and/or processes and/or elements and/or functions of monitoring engine 1500 may be implemented by cover sensor assembly 1100, some of the monitoring engine 1500 may be implemented by mobile device 1200, and/or some may be implemented by monitoring server 1300. Respective implementations and/or portions and/or processes and/or elements and/or functions of monitoring engine 1500 may herein be referenced by labels 1150, 1250 and 1350 denoting "assembly monitoring engine", "mobile device monitoring engine" and "server monitoring engine", respectively, causing cover sensor assembly 1100, mobile device 1200 and/or monitoring server 1300 to operate as disclosed herein.

To simplify the discussion that follows, methods and processes disclosed herein may be outlined herein in conjunction with monitoring engine 1500. Monitoring engine 1500 may be realized by one or more hardware, software and/or hybrid hardware/software modules, e.g., as outlined herein.

In an embodiment, validated physiological information may be transmitted in parallel to mobile device 1200 and server 1300. Monitoring system 1000 may include a communication layer for connecting an authentication layer for protecting data descriptive of the user's ID user and for securely transmitting data descriptive of physiological information to server 1300.

Monitoring system 1000 may allow uploading of data to server 1300 from millions of mobile devices having cover sensor assembly installed. Monitoring system 1000 may further include a web-portal which allows users to track the data collected by their personal cover sensor assembly, a CRM system to support customer and service provider interfaces (like doctors, and health services). Server 1300 may be operative to analyze the uploaded data, provide the user with trends related to his/her health and alerts in case the system detects problem.

Further referring to FIG. 5, a method for monitoring physiological parameters may include, as indicated by box 510, subjecting a physiological sensor to a sensor stimuli relating to physiological information about a user of a monitoring system and generating data ("physiological data") descriptive of the sensor stimuli. For example, monitoring system 1000 may receive such physiological data from the user via one or more of physiological sensors 1110A-1110G.

In an embodiment, the method may further include, as indicated by box 520, determining if the conditions are met for displaying to the user the physiological information, e.g., by employing one or more of validation sensors 1120.

In an embodiment, the method may include, as indicated by box 530, displaying the user of the monitoring system the physiological information if the conditions are met.

The various features and steps discussed above, as well as other known equivalents for each such feature or step, can be mixed and matched by one of ordinary skill in this art to perform methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein. For example, any digital computer engine (exemplified herein as monitoring engine 1500) can be configured or otherwise programmed to implement a method disclosed herein, and to the extent that a particular digital computer system is configured to implement such a method, it is within the scope and spirit of the disclosure. Once a digital computer system is programmed to perform particular functions pursuant to computer-executable instructions from program software that implements a method disclosed herein, it in effect becomes a special purpose computer particular to an embodiment of the method disclosed herein. The techniques necessary to achieve this are well known to those skilled in the art and thus are not further described herein. The methods and/or processes disclosed herein may be implemented as a computer program product such as, for example, a computer program tangibly embodied in an information carrier, for example, in a non-transitory computer-readable or non-transitory machine-readable storage device and/or in a propagated signal, for execution by or to control the operation of, a data processing apparatus including, for example, one or more programmable processors and/or one or more computers. The terms "non-transitory computer-readable storage device" and "non-transitory machine-readable storage device" encompasses distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by a communication network.

In the discussion, unless otherwise stated, adjectives such as "substantially" and "about" that modify a condition or relationship characteristic of a feature or features of an embodiment of the invention, are to be understood to mean that the condition or characteristic is defined to within tolerances that are acceptable for operation of the embodiment for an application for which it is intended.

Positional terms such as "upper", "lower" "right", "left", "bottom", "below", "lowered", "low", "top", "above", "elevated", "high", "vertical" and "horizontal" as well as grammatical variations thereof as may be used herein do not necessarily indicate that, for example, a "bottom" component is below a "top" component, or that a component that is "below" is indeed "below" another component or that a component that is "above" is indeed "above" another component as such directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both.

"Coupled with" means indirectly or directly "coupled with".

Where applicable, although state diagrams, flow diagrams or both may be used to describe embodiments, the technique is not limited to those diagrams or to the corresponding descriptions. For example, flow need not move through each illustrated box or state, or in exactly the same order as illustrated and described.

What is claimed is:

1. A system for monitoring vital signs, configured to be used in conjunction with a computerized mobile device, the system comprising:
   a cover sensor assembly adapted to be operably engaged with the computerized mobile device, said cover sensor assembly having integrated therein multiple physiological sensors;
   a physiological data acquisition module configured to generate a physiological parameter measurement descriptive of one or more physiological parameters measured by physiological sensors;
   a plurality of validation sensors; and
   a validation module configured to:
   compare between readings of the plurality of the validation sensors; and
   automatically toggle, based on the readings of the plurality of validation sensors, between physiological sensors of the multiple physiological sensors that measure a same physiological parameter of the one or more physiological parameters.

2. The system of claim 1, further comprising at least one validation sensor of the plurality of validation sensors, positioned so as to be used in conjunction with said at least one physiological sensor and configured to provide validation data to said validation module to determine a validity status of said physiological parameter measurement.

3. The system of claim 2, wherein said at least one validation sensor configured to sense whether said at least one physiological sensor of the multiple physiological sensors is positioned to receive a physical stimulus in a valid manner.

4. The system of claim 3, wherein said at least one physiological sensor is a photoplethysmograph sensor and said at least one validation sensor is selected from a group of sensors including: a pressure sensor, a position sensor, a capacitance sensor, a conductance sensor.

5. The system of claim 1, wherein the multiple physiological sensors are selected from a group including: a temperature sensor, a heart rate sensor, an ECG sensor, a photoplethysmograph sensor, a blood pressure sensor and a blood composition sensor.

6. The system of claim 1, wherein said plurality of validation sensors are selected from a group of sensors including: a pressure sensor, a force sensor, a temperature sensor, an impedance sensor, a capacitance sensor, a torque sensor, an accelerometer, a barometer, a light sensor, proximity sensor, a position sensor, a conductance sensor and a humidity sensor.

7. The system of claim 1, wherein the multiple physiological sensors comprises a photoplethysmograph sensor; wherein the plurality of validation sensors comprise a temperature sensor, and wherein the system is configured to correct for variations in oxygen saturations readings influenced by a temperature of a tissue area that engages with the photoplethysmograph sensor.

8. The system of claim 7, wherein at least one validation sensor of the plurality of validation sensors is built into a location on said cover sensor assembly selected from a group comprising: a backside, a front side and a sidewall.

9. The system of claim 1, comprising at least one validation sensor of the plurality of validation sensors, wherein said at least one validation sensor is integrated into said cover sensor assembly.

10. The system of claim 1, comprising the plurality of validation sensors; at least one of which is integrated into the computerized mobile device operably engaged with said cover sensor assembly.

11. The system of claim 1, comprising the plurality of said validation sensors, at least one of said plurality of validation sensors is integrated into said cover sensor assembly and at least one of said plurality of validation sensors is integrated into the computerized mobile device operably engaged with said cover sensor assembly.

12. The system of claim 1, wherein at least one of the multiple physiological sensors is integrated in the computerized mobile device.

13. The system of claim 12, wherein said at least one physiological sensor includes a capacitive touch screen of the computerized mobile device.

14. The system of claim 1, wherein at least one physiological sensor of the multiple physiological sensors is built into a location on said cover sensor assembly selected from a group comprising: a backside, a front side and a sidewall.

* * * * *